United States Patent
Jimenez et al.

(10) Patent No.: US 10,842,620 B2
(45) Date of Patent: Nov. 24, 2020

(54) SYSTEMS AND METHODS FOR ANCHORING AND SEALING A PROSTHETIC HEART VALVE

(71) Applicant: Edwards Lifesciences CardiAQ LLC, Irvine, CA (US)

(72) Inventors: Jorge H. Jimenez, Atlanta, GA (US); James L. Greene, Warwickshire (GB)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 147 days.

(21) Appl. No.: 16/143,130

(22) Filed: Sep. 26, 2018

(65) Prior Publication Data

US 2019/0021855 A1    Jan. 24, 2019

Related U.S. Application Data

(63) Continuation of application No. 15/191,054, filed on Jun. 23, 2016, now Pat. No. 10,092,400.

(Continued)

(51) Int. Cl.
*A61F 2/24* (2006.01)

(52) U.S. Cl.
CPC .......... *A61F 2/2418* (2013.01); *A61F 2/2436* (2013.01); *A61F 2220/0008* (2013.01); *A61F 2230/0034* (2013.01); *A61F 2250/0018* (2013.01)

(58) Field of Classification Search
CPC .... A61F 2/2418; A61F 2/2412; A61F 2/2427; A61F 2/2436; A61F 2/2439; A61F 2/966; A61F 2/852; A61F 2002/9534

See application file for complete search history.

(56) References Cited

U.S. PATENT DOCUMENTS

| | | |
|---|---|---|
| 3,657,744 A | 4/1972 | Ersek |
| 3,671,979 A | 6/1972 | Moulopoulos |

(Continued)

FOREIGN PATENT DOCUMENTS

| | | |
|---|---|---|
| CA | 2304325 A1 | 10/2000 |
| CA | 2827556 A1 | 7/2012 |

(Continued)

OTHER PUBLICATIONS

Bavaria, Joseph E. M.D. et al.: "Transcatheter Mitral Valve Implantation: The Future Gold Standard for MR?," Applicant requests the Examiner to consider this reference as of Dec. 2010.

(Continued)

*Primary Examiner* — Brian A Dukert
(74) *Attorney, Agent, or Firm* — Klarquist Sparkman LLP

(57) ABSTRACT

A method of implanting a prosthetic heart valve includes advancing a prosthetic heart valve to an implantation location within a patient's body, positioning the prosthetic heart valve within a native heart valve annulus, expanding a frame of the prosthetic heart valve from a first contracted configuration to a first expanded configuration, and then contracting the frame to a second contracted configuration. The prosthetic heart valve may be repositioned and then re-expanded from the second contracted configuration to a second expanded configuration. The prosthetic heart valve is preferably released from the delivery apparatus while in the second expanded configuration. Releasing the prosthetic heart valve from the delivery apparatus may result in radial expansion of a flange portion of the prosthetic heart valve.

10 Claims, 13 Drawing Sheets

Related U.S. Application Data

(60) Provisional application No. 62/183,562, filed on Jun. 23, 2015.

(56) References Cited

U.S. PATENT DOCUMENTS

| | | | |
|---|---|---|---|
| 3,739,402 | A | 6/1973 | Cooley et al. |
| 4,056,854 | A | 11/1977 | Boretos et al. |
| 4,079,468 | A | 3/1978 | Liotta et al. |
| 4,204,283 | A | 5/1980 | Bellhouse et al. |
| 4,222,126 | A | 9/1980 | Boretos et al. |
| 4,265,694 | A | 5/1981 | Boretos et al. |
| 4,339,831 | A | 7/1982 | Johnson |
| 4,340,977 | A | 7/1982 | Brownlee et al. |
| 4,470,157 | A | 9/1984 | Love |
| 4,477,930 | A | 10/1984 | Totten et al. |
| 4,490,859 | A | 1/1985 | Black et al. |
| 4,553,545 | A | 11/1985 | Maass et al. |
| 4,777,951 | A | 10/1988 | Cribier et al. |
| 4,865,600 | A | 9/1989 | Carpentier et al. |
| 4,994,077 | A | 2/1991 | Dobben |
| 5,326,371 | A | 7/1994 | Love et al. |
| 5,332,402 | A | 7/1994 | Teitelbaum |
| 5,370,685 | A | 12/1994 | Stevens |
| 5,415,667 | A | 5/1995 | Frater |
| 5,545,214 | A | 8/1996 | Stevens |
| 5,554,183 | A | 9/1996 | Nazari |
| 5,554,185 | A | 9/1996 | Block et al. |
| 5,697,382 | A | 12/1997 | Love et al. |
| 5,797,951 | A | 8/1998 | Mueller |
| 5,840,081 | A | 11/1998 | Andersen et al. |
| 5,855,601 | A | 1/1999 | Bessler et al. |
| 5,957,949 | A | 9/1999 | Leonhardt et al. |
| 6,086,612 | A | 7/2000 | Jansen |
| 6,113,631 | A | 9/2000 | Jansen |
| 6,168,614 | B1 | 1/2001 | Andersen et al. |
| 6,224,626 | B1 | 5/2001 | Steinke |
| 6,251,093 | B1 | 6/2001 | Valley et al. |
| 6,267,783 | B1 | 7/2001 | Letendre et al. |
| 6,312,465 | B1 | 11/2001 | Griffin et al. |
| 6,358,277 | B1 | 3/2002 | Duran |
| 6,440,164 | B1 | 8/2002 | DiMatteo et al. |
| 6,458,153 | B1 | 10/2002 | Bailey et al. |
| 6,482,228 | B1 | 11/2002 | Norred |
| 6,527,800 | B1 | 3/2003 | McGuckin, Jr. et al. |
| 6,558,396 | B1 | 5/2003 | Inoue |
| 6,582,462 | B1 | 6/2003 | Andersen et al. |
| 6,610,088 | B1 | 8/2003 | Gabbay |
| 6,629,534 | B1 | 10/2003 | St. Goar et al. |
| 6,652,578 | B2 | 11/2003 | Bailey et al. |
| 6,656,215 | B1 | 12/2003 | Yanez et al. |
| 6,669,720 | B1 | 12/2003 | Pierce |
| 6,676,698 | B2 | 1/2004 | McGuckin, Jr. et al. |
| 6,695,878 | B2 | 2/2004 | McGuckin, Jr. et al. |
| 6,712,836 | B1 | 3/2004 | Berg et al. |
| 6,716,207 | B2 | 4/2004 | Farnholtz |
| 6,716,230 | B2 | 4/2004 | Whitman |
| 6,729,356 | B1 | 5/2004 | Baker et al. |
| 6,730,118 | B2 | 5/2004 | Spenser et al. |
| 6,730,121 | B2 | 5/2004 | Ortiz et al. |
| 6,733,525 | B2 | 5/2004 | Yang et al. |
| 6,746,422 | B1 | 6/2004 | Noriega et al. |
| 6,749,560 | B1 | 6/2004 | Konstorum et al. |
| 6,761,733 | B2 | 7/2004 | Chobotov et al. |
| 6,767,362 | B2 | 7/2004 | Schreck |
| 6,773,456 | B1 | 8/2004 | Gordon et al. |
| 6,780,200 | B2 | 8/2004 | Jansen |
| 6,790,229 | B1 | 9/2004 | Berrekouw |
| 6,790,230 | B2 | 9/2004 | Beyersdorf et al. |
| 6,860,900 | B2 | 3/2005 | Clerc et al. |
| 6,875,231 | B2 | 4/2005 | Anduiza et al. |
| 6,890,350 | B1 | 5/2005 | Walak |
| 6,893,460 | B2 | 5/2005 | Spenser et al. |
| 6,908,481 | B2 | 6/2005 | Cribier |
| 6,929,659 | B2 | 8/2005 | Pinchuk |
| 6,945,994 | B2 | 9/2005 | Austin et al. |
| 6,951,571 | B1 | 10/2005 | Srivastava |
| 7,007,396 | B2 | 3/2006 | Rudko et al. |
| 7,011,681 | B2 | 3/2006 | Vesely |
| 7,018,406 | B2 | 3/2006 | Seguin et al. |
| 7,041,132 | B2 | 5/2006 | Quijano et al. |
| 7,090,688 | B2 | 8/2006 | Nishtala et al. |
| 7,097,658 | B2 | 8/2006 | Oktay |
| 7,141,063 | B2 | 11/2006 | White et al. |
| 7,186,265 | B2 | 3/2007 | Sharkawy et al. |
| 7,192,440 | B2 | 3/2007 | Andreas et al. |
| 7,198,646 | B2 | 4/2007 | Figulla et al. |
| 7,201,772 | B2 | 4/2007 | Schwammenthal et al. |
| 7,276,078 | B2 | 10/2007 | Spenser et al. |
| 7,329,278 | B2 | 2/2008 | Seguin et al. |
| 7,381,219 | B2 | 6/2008 | Salahieh et al. |
| 7,393,360 | B2 | 7/2008 | Spenser et al. |
| 7,429,269 | B2 | 9/2008 | Schwammenthal et al. |
| 7,442,204 | B2 | 10/2008 | Schwammenthal et al. |
| 7,445,631 | B2 | 11/2008 | Salahieh et al. |
| 7,462,191 | B2 | 12/2008 | Spenser et al. |
| 7,510,575 | B2 | 3/2009 | Spenser et al. |
| 7,524,330 | B2 | 4/2009 | Berreklouw |
| 7,553,324 | B2 | 6/2009 | Andreas et al. |
| 7,585,321 | B2 | 9/2009 | Cribier |
| 7,618,446 | B2 | 11/2009 | Andersen et al. |
| 7,621,948 | B2 | 11/2009 | Herrmann et al. |
| 7,628,805 | B2 | 12/2009 | Spenser et al. |
| 7,748,389 | B2 | 7/2010 | Salahieh et al. |
| 7,753,949 | B2 | 7/2010 | Lamphere et al. |
| 7,803,185 | B2 | 9/2010 | Gabbay |
| 7,806,919 | B2 | 10/2010 | Bloom et al. |
| 7,815,673 | B2 | 10/2010 | Bloom et al. |
| 7,824,443 | B2 | 11/2010 | Salahieh et al. |
| 7,892,281 | B2 | 2/2011 | Seguin et al. |
| 7,914,569 | B2 | 3/2011 | Nguyen et al. |
| 7,947,075 | B2 | 5/2011 | Goetz et al. |
| 7,959,672 | B2 | 6/2011 | Salahieh et al. |
| 7,972,378 | B2 | 7/2011 | Tabor et al. |
| 7,981,151 | B2 | 7/2011 | Rowe |
| 7,993,392 | B2 | 8/2011 | Righini et al. |
| 7,993,394 | B2 | 8/2011 | Hariton et al. |
| 8,016,877 | B2 | 9/2011 | Seguin et al. |
| 8,048,153 | B2 | 11/2011 | Salahieh et al. |
| 8,052,750 | B2 | 11/2011 | Tuval et al. |
| 8,070,800 | B2 | 12/2011 | Look et al. |
| 8,070,802 | B2 | 12/2011 | Lamphere et al. |
| 8,075,615 | B2 | 12/2011 | Eberhardt et al. |
| 8,080,054 | B2 | 12/2011 | Rowe |
| 8,092,520 | B2 | 1/2012 | Quadri |
| 8,109,996 | B2 | 2/2012 | Stacchino et al. |
| 8,118,866 | B2 | 2/2012 | Herrmann et al. |
| 8,136,218 | B2 | 3/2012 | Millwee et al. |
| 8,137,398 | B2 | 3/2012 | Tuval et al. |
| 8,157,852 | B2 | 4/2012 | Bloom et al. |
| 8,167,934 | B2 | 5/2012 | Styrc et al. |
| 8,182,528 | B2 | 5/2012 | Salahieh et al. |
| 8,182,530 | B2 | 5/2012 | Huber |
| 8,216,301 | B2 | 7/2012 | Bonhoeffer et al. |
| 8,219,229 | B2 | 7/2012 | Cao et al. |
| 8,220,121 | B2 | 7/2012 | Hendriksen et al. |
| 8,221,493 | B2 | 7/2012 | Boyle et al. |
| 8,226,710 | B2 | 7/2012 | Nguyen et al. |
| 8,236,045 | B2 | 8/2012 | Benichou et al. |
| 8,246,675 | B2 | 8/2012 | Zegdi |
| 8,246,678 | B2 | 8/2012 | Salahieh et al. |
| 8,252,036 | B2 | 8/2012 | Cartledge et al. |
| 8,252,051 | B2 | 8/2012 | Chau et al. |
| 8,252,052 | B2 | 8/2012 | Salahieh et al. |
| 8,287,584 | B2 | 10/2012 | Salahieh et al. |
| 8,303,653 | B2 | 11/2012 | Bonhoeffer et al. |
| 8,313,525 | B2 | 11/2012 | Tuval et al. |
| 8,323,335 | B2 | 12/2012 | Rowe et al. |
| 8,353,953 | B2 | 1/2013 | Giannetti et al. |
| 8,403,983 | B2 | 3/2013 | Quadri et al. |
| 8,414,644 | B2 | 4/2013 | Quadri et al. |
| 8,414,645 | B2 | 4/2013 | Dwork et al. |
| 8,444,689 | B2 | 5/2013 | Zhang |
| 8,449,599 | B2 | 5/2013 | Chau et al. |
| 8,454,685 | B2 | 6/2013 | Hariton et al. |

(56) References Cited

U.S. PATENT DOCUMENTS

| | | |
|---|---|---|
| 8,460,368 B2 | 6/2013 | Taylor et al. |
| 8,470,023 B2 | 6/2013 | Eidenschink et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,096 B2 | 8/2013 | Nelson |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,597,348 B2 | 12/2013 | Rowe et al. |
| 8,617,236 B2 | 12/2013 | Paul et al. |
| 8,640,521 B2 | 2/2014 | Righini et al. |
| 8,647,378 B2 | 2/2014 | Mews et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,668,733 B2 | 3/2014 | Haug et al. |
| 8,673,000 B2 | 3/2014 | Tabor et al. |
| 8,673,001 B2 | 3/2014 | Cartledge et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,708 B2 | 5/2014 | Seguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,758,432 B2 | 6/2014 | Solem |
| 8,764,818 B2 | 7/2014 | Gregg |
| 8,771,344 B2 | 7/2014 | Tran et al. |
| 8,771,345 B2 | 7/2014 | Tuval et al. |
| 8,771,346 B2 | 7/2014 | Tuval et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,356 B2 | 8/2014 | Quadri et al. |
| 8,795,357 B2 | 8/2014 | Yohanan et al. |
| 8,808,356 B2 | 8/2014 | Braido et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,845,718 B2 | 9/2014 | Tuval et al. |
| 8,858,620 B2 | 10/2014 | Salahieh et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,911,455 B2 | 12/2014 | Quadri et al. |
| 8,926,693 B2 | 1/2015 | Duffy et al. |
| 8,926,694 B2 | 1/2015 | Costello |
| 8,939,960 B2 | 1/2015 | Rosenman et al. |
| 8,945,209 B2 | 2/2015 | Bonyuet et al. |
| 8,951,299 B2 | 2/2015 | Paul et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,372 B2 | 3/2015 | Murry, III et al. |
| 8,986,375 B2 | 3/2015 | Garde et al. |
| 8,992,608 B2 | 3/2015 | Haug et al. |
| 8,998,979 B2 | 4/2015 | Seguin et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,034,033 B2 | 5/2015 | McLean et al. |
| 9,039,757 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| 9,173,737 B2 | 11/2015 | Hill et al. |
| 9,180,004 B2 | 11/2015 | Alkhatib |
| 9,186,249 B2 | 11/2015 | Rolando et al. |
| 9,220,594 B2 | 12/2015 | Braido et al. |
| 9,241,790 B2 | 1/2016 | Lane et al. |
| 9,248,014 B2 | 2/2016 | Lane et al. |
| 9,277,990 B2 | 3/2016 | Klima et al. |
| 9,277,993 B2 | 3/2016 | Gamarra et al. |
| 9,289,291 B2 | 3/2016 | Gorman, III et al. |
| 9,289,296 B2 | 3/2016 | Braido et al. |
| 9,295,551 B2 | 3/2016 | Straubinger et al. |
| 9,326,815 B2 | 5/2016 | Watson |
| 9,331,328 B2 | 5/2016 | Eberhardt et al. |
| 9,339,382 B2 | 5/2016 | Tabor et al. |
| 9,351,831 B2 | 5/2016 | Braido et al. |
| 9,351,832 B2 | 5/2016 | Braido et al. |
| 9,364,321 B2 | 6/2016 | Alkhatib et al. |
| 9,445,897 B2 | 9/2016 | Bishop et al. |
| 9,456,877 B2 | 10/2016 | Weitzner et al. |
| 9,681,968 B2 | 6/2017 | Goetz et al. |
| 9,700,329 B2 | 7/2017 | Metzger et al. |
| 9,700,411 B2 | 7/2017 | Klima et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0077695 A1 | 6/2002 | Swanson et al. |
| 2003/0105517 A1 | 6/2003 | White et al. |
| 2003/0120331 A1 | 6/2003 | Chobotov et al. |
| 2003/0120333 A1 | 6/2003 | Ouriel et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0117009 A1 | 6/2004 | Cali et al. |
| 2004/0133273 A1 | 7/2004 | Cox |
| 2004/0186561 A1 | 9/2004 | McGuckin et al. |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |

(56) References Cited

U.S. PATENT DOCUMENTS

| | | |
|---|---|---|
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2006/0020327 A1 | 1/2006 | Lashinski et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0173527 A1 | 8/2006 | Scherrible |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0241745 A1 | 10/2006 | Solem |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0010876 A1 | 1/2007 | Salahieh et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0255394 A1 | 11/2007 | Ryan |
| 2008/0009746 A1 | 1/2008 | Forster et al. |
| 2008/0021546 A1 | 1/2008 | Patz et al. |
| 2008/0071366 A1 | 3/2008 | Tuval et al. |
| 2008/0082164 A1 | 4/2008 | Friedman |
| 2008/0082165 A1 | 4/2008 | Wilson et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0228254 A1 | 9/2008 | Ryan |
| 2009/0005863 A1 | 1/2009 | Goetz et al. |
| 2009/0030501 A1 | 1/2009 | Morris et al. |
| 2009/0099653 A1 | 4/2009 | Suri et al. |
| 2009/0138079 A1 | 5/2009 | Tuval et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0292350 A1 | 11/2009 | Eberhardt et al. |
| 2009/0306768 A1 | 12/2009 | Quadri |
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0305685 A1 | 12/2010 | Millwee et al. |
| 2011/0004296 A1 | 1/2011 | Lutter et al. |
| 2011/0029067 A1 | 2/2011 | McGuckin, Jr. et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2011/0313515 A1 | 12/2011 | Quadri et al. |
| 2012/0022639 A1 | 1/2012 | Hacohen et al. |
| 2012/0041550 A1 | 2/2012 | Salahieh et al. |
| 2012/0059454 A1 | 3/2012 | Millwee et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0215303 A1 | 8/2012 | Quadri et al. |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2012/0323316 A1 | 12/2012 | Chau et al. |
| 2013/0006294 A1 | 1/2013 | Kashkarov et al. |
| 2013/0035759 A1 | 2/2013 | Gross et al. |
| 2013/0046373 A1 | 2/2013 | Cartledge et al. |
| 2013/0053950 A1 | 2/2013 | Rowe et al. |
| 2013/0131788 A1 | 5/2013 | Quadri et al. |
| 2013/0144378 A1 | 6/2013 | Quadri et al. |
| 2013/0166017 A1* | 6/2013 | Cartledge ............... A61F 2/82 623/1.15 |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214159 A1 | 7/2014 | Vidlund et al. |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0222144 A1 | 8/2014 | Eberhardt et al. |
| 2014/0230515 A1 | 8/2014 | Tuval et al. |
| 2014/0236288 A1 | 8/2014 | Lambrecht et al. |
| 2014/0257467 A1 | 9/2014 | Lane et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |

(56) References Cited

U.S. PATENT DOCUMENTS

| | | |
|---|---|---|
| 2014/0379068 A1 | 12/2014 | Thielen et al. |
| 2014/0379077 A1 | 12/2014 | Tuval et al. |
| 2015/0005863 A1 | 1/2015 | Para |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0142103 A1 | 5/2015 | Vidlund |
| 2015/0148731 A1 | 5/2015 | McNamara et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0297346 A1 | 10/2015 | Duffy et al. |
| 2015/0327994 A1 | 11/2015 | Morriss et al. |
| 2015/0328001 A1 | 11/2015 | McLean et al. |
| 2015/0335429 A1 | 11/2015 | Morriss et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0279386 A1 | 9/2016 | Dale et al. |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325954 A1 | 11/2017 | Perszyk |
| 2017/0348096 A1 | 12/2017 | Anderson |
| 2017/0367823 A1 | 12/2017 | Hariton et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |

FOREIGN PATENT DOCUMENTS

| | | |
|---|---|---|
| DE | 102006052564 B3 | 12/2007 |
| EP | 1171059 A1 | 1/2002 |
| EP | 1369098 A1 | 12/2003 |
| EP | 1259194 B1 | 2/2005 |
| EP | 1255510 B1 | 4/2007 |
| EP | 1827558 A2 | 9/2007 |
| EP | 1239901 B1 | 10/2007 |
| EP | 1472996 B1 | 9/2009 |
| EP | 1935377 B1 | 3/2010 |
| EP | 2238947 A2 | 10/2010 |
| EP | 2308425 A1 | 4/2011 |
| EP | 2398543 A1 | 12/2011 |
| EP | 1281375 B1 | 2/2012 |
| EP | 2496182 A1 | 9/2012 |
| EP | 2285317 B1 | 12/2012 |
| EP | 2566416 A1 | 3/2013 |
| EP | 2319458 B1 | 4/2013 |
| EP | 2124826 B1 | 7/2014 |
| EP | 2750630 A1 | 7/2014 |
| EP | 2777617 A1 | 9/2014 |
| EP | 2745805 B1 | 6/2015 |
| EP | 2749254 B1 | 6/2015 |
| EP | 2898858 A1 | 7/2015 |
| EP | 1734903 B1 | 10/2015 |
| EP | 2967858 A2 | 1/2016 |
| EP | 2926766 B1 | 2/2016 |
| EP | 2985006 A1 | 2/2016 |
| EP | 2168536 B1 | 4/2016 |
| EP | 2815725 B1 | 4/2016 |
| EP | 2237746 B1 | 5/2016 |
| EP | 2815723 B1 | 7/2016 |
| EP | 2262451 B1 | 5/2017 |
| EP | 3184083 A1 | 6/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3294220 A1 | 3/2018 |
| GB | 1264471 A | 2/1972 |
| GB | 1315844 A | 5/1973 |
| GB | 2398245 A | 8/2004 |
| JP | 2002540889 A | 12/2002 |
| JP | 2008541865 A | 11/2008 |
| WO | 0061034 A1 | 10/2000 |
| WO | 03092554 A1 | 11/2003 |
| WO | 2004030569 A2 | 4/2004 |
| WO | 2005011534 A1 | 2/2005 |
| WO | 2006070372 A2 | 7/2006 |
| WO | 2006085225 A1 | 8/2006 |
| WO | 2006089236 A1 | 8/2006 |
| WO | 2006127765 A1 | 11/2006 |
| WO | 2007025028 A1 | 3/2007 |
| WO | 2007058857 A2 | 5/2007 |
| WO | 2007123658 A1 | 11/2007 |
| WO | 2008013915 A2 | 1/2008 |
| WO | 2008070797 A2 | 6/2008 |
| WO | 2008103722 A2 | 8/2008 |
| WO | 2008125153 A1 | 10/2008 |
| WO | 2008150529 A1 | 12/2008 |
| WO | 2009026563 A2 | 2/2009 |
| WO | 2009033469 A1 | 3/2009 |
| WO | 2009045331 A1 | 4/2009 |
| WO | 2009053497 A1 | 4/2009 |
| WO | 2009091509 A1 | 7/2009 |
| WO | 2009094500 A1 | 7/2009 |
| WO | 2009134701 A2 | 11/2009 |
| WO | 2010005524 A2 | 1/2010 |
| WO | 2010008549 A1 | 1/2010 |
| WO | 2010022138 A2 | 2/2010 |
| WO | 2010037141 A1 | 4/2010 |
| WO | 2010040009 A1 | 4/2010 |
| WO | 2010055262 A1 | 5/2010 |
| WO | 2011025945 A1 | 3/2011 |
| WO | 2011057087 A1 | 5/2011 |
| WO | 2011111047 A2 | 9/2011 |
| WO | 2011137531 A1 | 11/2011 |
| WO | 2012177942 A2 | 12/2012 |
| WO | 2013028387 A2 | 2/2013 |
| WO | 2013059747 A1 | 4/2013 |
| WO | 2013075215 A1 | 5/2013 |
| WO | 2013120181 A1 | 8/2013 |
| WO | 2013175468 A2 | 11/2013 |
| WO | 2013192305 A2 | 12/2013 |
| WO | 2014018432 A1 | 1/2014 |
| WO | 2014099655 A1 | 6/2014 |
| WO | 2014110019 A1 | 7/2014 |
| WO | 2014110171 A2 | 7/2014 |
| WO | 2014121042 A1 | 8/2014 |
| WO | 2014139545 A1 | 9/2014 |
| WO | 2014145338 A1 | 9/2014 |
| WO | 2014149865 A1 | 9/2014 |
| WO | 2014163706 A1 | 10/2014 |
| WO | 2014164364 A1 | 10/2014 |
| WO | 2014194178 A1 | 12/2014 |
| WO | 2014204807 A1 | 12/2014 |
| WO | 2014205064 A1 | 12/2014 |
| WO | 2015077274 A1 | 5/2015 |

(56) References Cited

FOREIGN PATENT DOCUMENTS

| WO | 2015148241 A1 | 10/2015 |
|---|---|---|
| WO | 2016016899 A1 | 2/2016 |

OTHER PUBLICATIONS

Boudjemline, Younes, et al., "Steps Toward the Percutaneous Replacement of Atrioventricular Valves," JACC, vol. 46, No. 2, Jul. 19, 2005:360-5.

Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.

Karimi, Houshang, et al., "Percutaneous Valve Therapies," SIS 2007 Yearbook, Chapter 11, pp. 1-11.

Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.

Ma, Liang, et al., "'Double-Crowned Valved Stents For Off-Pump Mitral Valve Replacement," European Journal of Cardio-thoracic Surgery 28 (2005) 194-199, Applicant believes this may have been available as early as Aug. 2005.

Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.

NJ350: Vote for Your Favorite New Jersey Innovations, Jun. 27, 2014, http://www.kilmerhouse.com/2014/06/nj350-vote-for-your-favorite-new-jersey-innovations/.

Pluth, James R., M.D., et al., "Aortic and Mitral Valve Replacement with Cloth-Covered Braunwald-Cutter Prosthesis, A Three-Year Follow-up," The Annals Of Thoracic Surgery, vol. 20, No. 3, Sep. 1975, pp. 239-248.

Spillner, J. et al., "New Sutureless 'Atrial- Mitral-Valve Prosthesis' For Minimally Invasive Mitral Valve Therapy," Textile Research Journal, 2010, in 7 pages, Applicant believes this may have been available as early as Aug. 9, 2010.

* cited by examiner

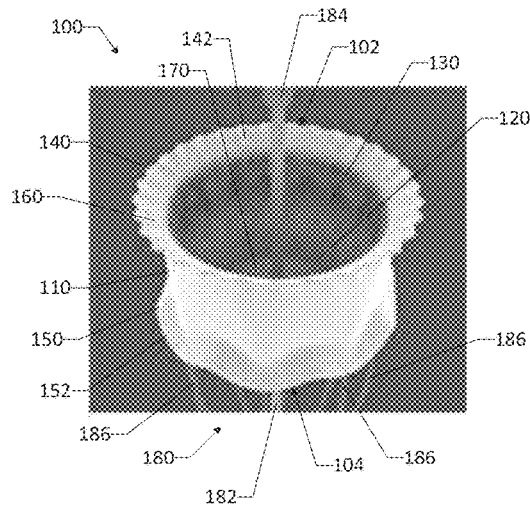
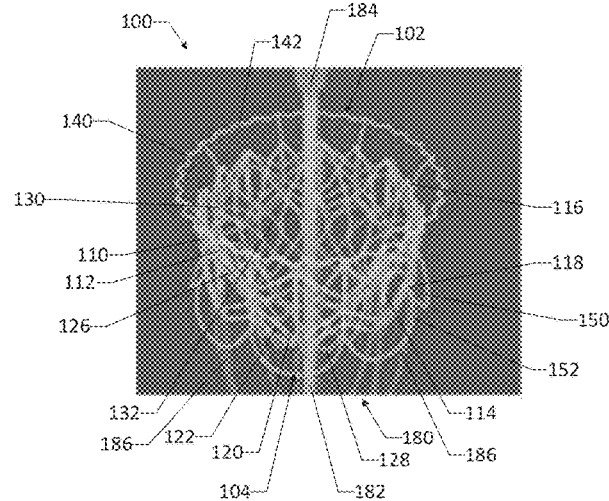
FIG. 1C                    FIG. 1D

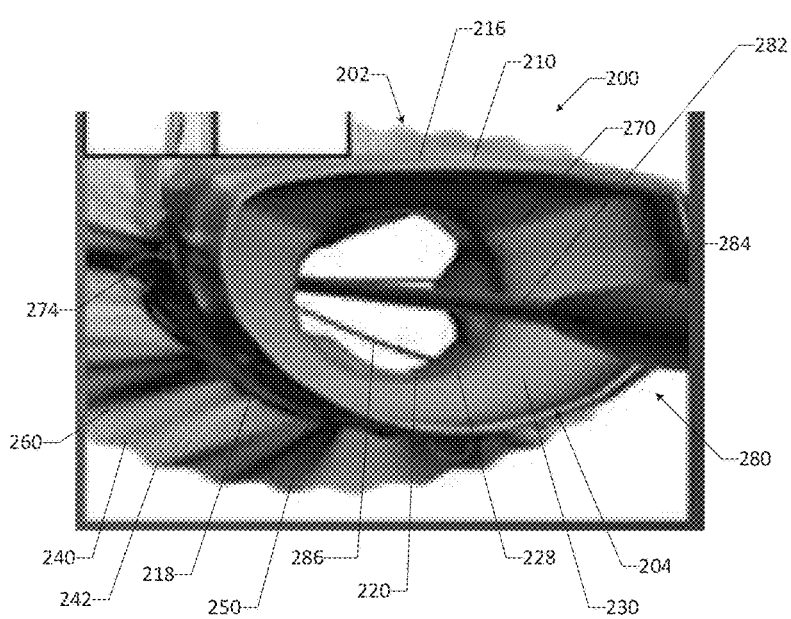
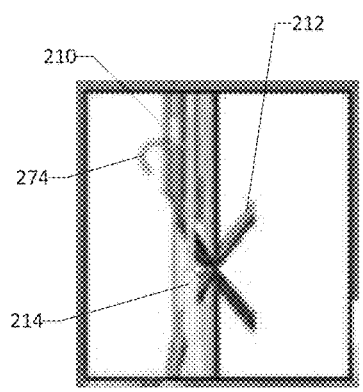
FIG. 2E
FIG. 2F

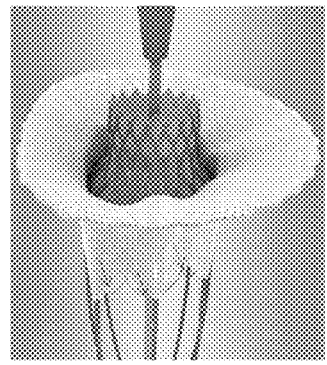
FIG. 3I
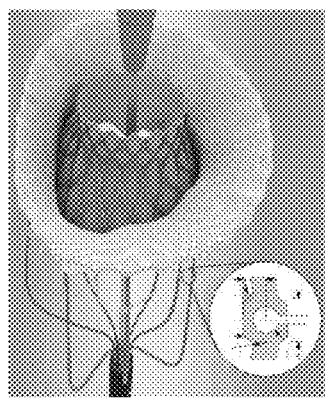
FIG. 3H
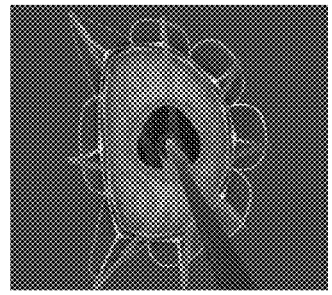
FIG. 3G
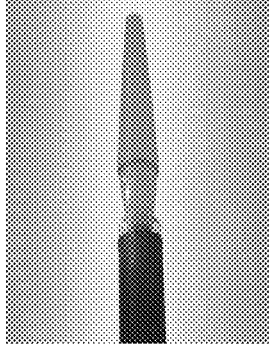
FIG. 3L
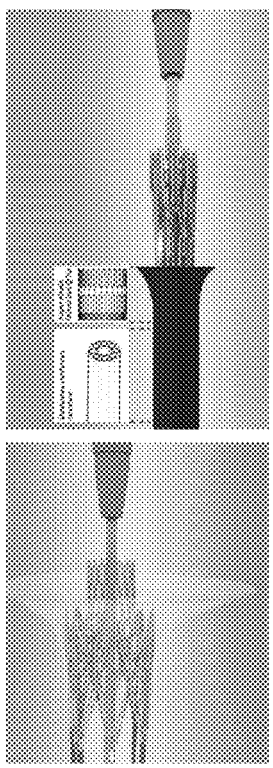
FIG. 3K
FIG. 3J

SYSTEMS AND METHODS FOR ANCHORING AND SEALING A PROSTHETIC HEART VALVE

CROSS-REFERENCE TO RELATED APPLICATIONS

This application is a continuation of U.S. application Ser. No. 15/191,054, filed Jun. 23, 2016, which claims the benefit of U.S. Provisional Application No. 62/183,562, filed Jun. 23, 2015. Each related application is incorporated by reference herein.

FIELD OF THE DISCLOSURE

The present disclosure relates generally to prosthetic heart valves and methods for replacing diseased or defective native heart valves, and more particularly to an expandable prosthetic heart valve including features for anchoring and sealing the prosthetic heart valve onto a native human heart and related methods for implanting the prosthetic heart valve to replace a diseased or defective native heart valve.

BACKGROUND OF THE DISCLOSURE

Various types of prosthetic heart valves are commonly used in valve replacement surgery to replace a diseased or defective native heart valve, such as an aortic valve, a mitral valve, a pulmonary valve, or a tricuspid valve, of a native human heart. A prosthetic heart valve generally may include a frame or other support structure configured for positioning at an implantation site at or near the native heart valve and anchoring onto the native heart, and an occluder member, such as a multi-leaflet valve, attached to the frame and configured for controlling blood flow through the prosthetic heart valve. Upon implantation of the prosthetic heart valve, the frame may maintain the relative position of the prosthetic heart valve within the native heart, and the occluder member may control blood flow in a manner similar to the native heart valve, thereby restoring desired function of the heart.

According to traditional procedures, heart valve replacement may be performed via open heart surgery, which may require cardiopulmonary bypass and may present a significant risk of certain complications. In recent years, less-invasive procedures for heart valve replacement have been developed, which may eliminate the need for cardiopulmonary bypass and may decrease the risk of complications as compared to open heart surgery. For example, certain prosthetic heart valves may be implanted via a transapical approach, a transatrial approach, a transfemoral approach, a transseptal approach, a subclavian approach, a direct aortic puncture approach, or other vascular access approaches. Each type of approach for implanting prosthetic heart valves may present certain benefits and drawbacks. For example, the transapical approach may provide a direct, "straight shot" approach for replacing certain native heart valves, may allow a physician to leverage past experience in performing transcatheter aortic valve replacement (TAVR) procedures, and may allow a physician to have high degree of control over the prosthetic heart valve and instruments used to implant the heart valve. However, the transapical approach may be challenging in certain patients due to poor tissue quality at the apex of the heart and/or a relatively large outer diameter of the prosthetic heart valve being implanted, may result in left ventricle dysfunction, may present issues of sub-valvular entanglement, and may be more invasive than other potential approaches.

The transatrial approach may provide a direct antegrade approach for replacing certain native heart valves, may avoid sub-valvular anatomy, may eliminate the need to puncture the left ventricle, and may be less sensitive to the size of the outer diameter of the prosthetic heart valve being implanted. However, the transatrial approach may present challenges in steering and navigating the prosthetic heart valve through the anatomy to the desired implantation site, may present a steep learning curve for a physician having experience only with the transapical approach, and may be more invasive than other potential approaches. The transseptal approach may provide a direct antegrade approach for replacing certain native heart valves, may eliminate the need to puncture the left ventricle, and may allow a physician to leverage past experience in performing other procedures through a transseptal puncture. However, the transseptal approach may present challenges in steering and navigating the prosthetic heart valve through the anatomy to the desired implantation site, may require a physician to deliver the prosthetic heart valve over a relatively long distance as compared to other potential approaches, may present challenges in patients having an atrial and/or septal defect, in particular when the prosthetic heart valve has a relatively large outer diameter, and may require venous or arterial access in order to deliver the prosthetic heart valve to the desired implantation site.

Currently, less-invasive approaches are most commonly used in performing aortic valve replacement procedures, although it would be desirable to use less-invasive approaches in replacing mitral valves, pulmonary valves, and/or tricuspid valves in a similar manner. In view of the differences between the aortic valve and the other native heart valves, however, prosthetic heart valves and related instruments configured for aortic valve replacement generally would not be suitable for replacing the other native heart valves. Accordingly, there remains a need for a prosthetic heart valve that is suitable for replacement of the mitral valve, the pulmonary valve, and/or the tricuspid valve. It will be appreciated that a prosthetic heart valve configured for mitral, pulmonary, and/or tricuspid valve replacement may require certain differences in design and function, as compared to prosthetic heart valves configured for aortic valve replacement, in order to be implanted via a less-invasive approach and to function in a suitable manner. In particular, such a prosthetic heart valve should accommodate or conform to the shape and structure of the native heart valve and/or surrounding anatomy without compromising the integrity or function of the surrounding anatomy or the occluder member of the prosthetic heart valve. Such a prosthetic heart valve also should securely anchor onto the native heart tissue to prevent or inhibit migration of the prosthetic heart valve from the implantation site. Further, such a prosthetic heart valve should form a seal against the native heart tissue to prevent or inhibit paravalvular leakage.

SUMMARY OF THE DISCLOSURE

Various embodiments described herein provide prosthetic heart valves and related methods for implanting a prosthetic heart valve to replace a diseased or defective native heart valve. According to one aspect, a prosthetic heart valve for replacing a diseased or defective native heart valve is provided. In one embodiment, the prosthetic heart valve may include an outer frame, an inner frame positioned at least partially within the outer frame, and an occluder member positioned at least partially within the inner frame. The prosthetic heart valve also may include an atrial flange extending from an atrial end of the outer frame, and a ventricular flange extending from a ventricular end of the outer frame, wherein at least a portion of the atrial flange extends radially outward beyond the ventricular flange.

In another embodiment, the prosthetic heart valve may include an outer frame having a D-shaped cross-sectional shape in a plane orthogonal to a longitudinal axis of the prosthetic heart valve, and an inner frame positioned at least partially within the outer frame and having a circular cross-sectional shape in the plane orthogonal to the longitudinal axis of the prosthetic heart valve. The prosthetic heart valve also may include an occluder member positioned at least partially within the inner frame, an atrial flange extending from an atrial end of the outer frame, and a ventricular flange extending from a ventricular end of the outer frame.

In still another embodiment, the prosthetic heart valve may include an expandable outer frame having a D-shaped cross-sectional shape in a plane orthogonal to a longitudinal axis of the prosthetic heart valve, and an expandable inner frame positioned at least partially within the outer frame and having a circular cross-sectional shape in the plane orthogonal to the longitudinal axis of the prosthetic heart valve. The prosthetic heart valve also may include an occluder member positioned at least partially within the inner frame, an atrial flange extending from an atrial end of the outer frame, and a ventricular flange extending from a ventricular end of the outer frame, wherein at least a portion of the atrial flange extends radially outward beyond the ventricular flange.

These and other aspects and embodiments of the present disclosure will be apparent or will become apparent to one of ordinary skill in the art upon review of the following detailed description when taken in conjunction with the several drawings and the appended claims.

BRIEF DESCRIPTION OF THE DRAWINGS

In describing the various embodiments of the present disclosure, reference is made to the accompanying drawings, which are not necessarily drawn to scale, and wherein:

FIG. 1C is a top perspective view of the prosthetic heart valve and a portion of the delivery device of FIG. 1A, showing the prosthetic heart valve in the expanded state.

FIG. 1D is a top perspective view of the outer frame, the inner frame, the atrial flange/skirt, and the ventricular flange/skirt of the prosthetic heart valve and a portion of the delivery device of FIG. 1A, showing the prosthetic heart valve in the expanded state.

FIG. 2E is a perspective view of a portion of the prosthetic heart valve of FIG. 2A and a portion of a delivery device attached to the prosthetic heart valve, showing the prosthetic heart valve in the expanded state and an anchor of the prosthetic heart valve in a deployed state.

FIG. 2F is a detailed side view of a portion of the prosthetic heart valve of FIG. 2A, showing the anchor of the prosthetic heart valve in the deployed state.

FIG. 3G is a top view of a prosthetic heart valve, beginning a series in FIGS. 3G-3L, showing how a single articulating operation minimizes complexity in re-sheathing atrial petals after deployment.

FIG. 3H is a bottom perspective view of the prosthetic heart valve of FIG. 3G showing how control wires pass outside or within slots in atrial petals to enable inward deflection.

FIG. 3I is a bottom perspective view of the prosthetic heart valve of FIG. 3G showing coordinated contraction of stent and forward motion of sheath to allow for petals to be retracted into the frame.

FIG. 3J is a side view of the prosthetic heart valve of FIG. 3G showing contraction and re-sheathing.

FIG. 3K is a side view of the prosthetic heart valve of FIG. 3G showing that the structure from a multi-lumen tube allows the use of wires to pull petals inward without damaging the tip.

FIG. 3L is a side view of the prosthetic heart valve of FIG. 3G showing the tip recoiling into a straight configuration after passing over the implant.

DETAILED DESCRIPTION OF THE DISCLOSURE

Figure 1A:
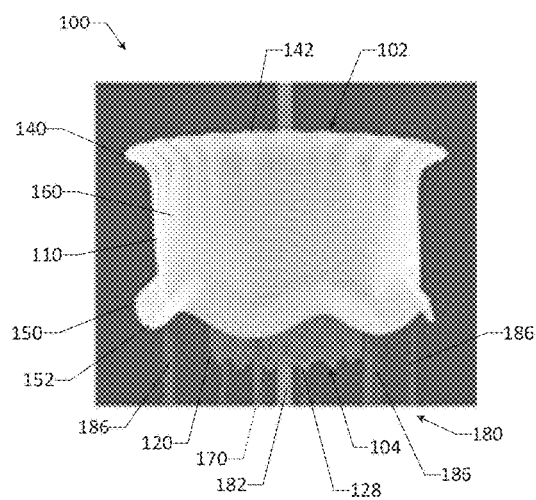
FIG. 1A is a side view of a prosthetic heart valve and a portion of a delivery device in accordance with one or more embodiments of the present disclosure, showing the prosthetic heart valve in an expanded state.
Figure 1B:
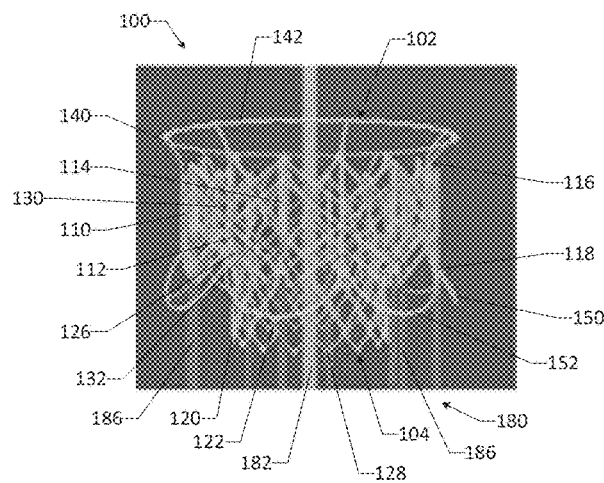
FIG. 1B is a side view of an outer frame, an inner frame, an atrial flange/skirt, and a ventricular flange/skirt of the prosthetic heart valve and a portion of the delivery device of FIG. 1A, showing the prosthetic heart valve in the expanded state.
Figure 1E:
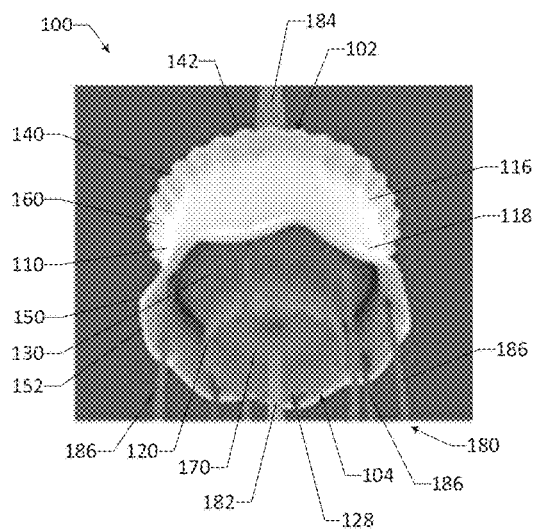
FIG. 1E is a bottom perspective view of the prosthetic heart valve and a portion of the delivery device of FIG. 1A, showing the prosthetic heart valve in the expanded state.
Figure 1F:
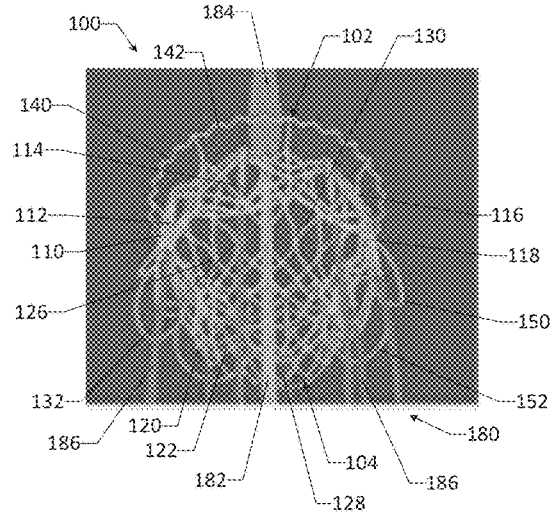
FIG. 1F is a bottom perspective view of the outer frame, the inner frame, the atrial flange/skirt, and the ventricular flange/skirt of the prosthetic heart valve and a portion of the delivery device of FIG. 1A, showing the prosthetic heart valve in the expanded state.
Figure 2A:
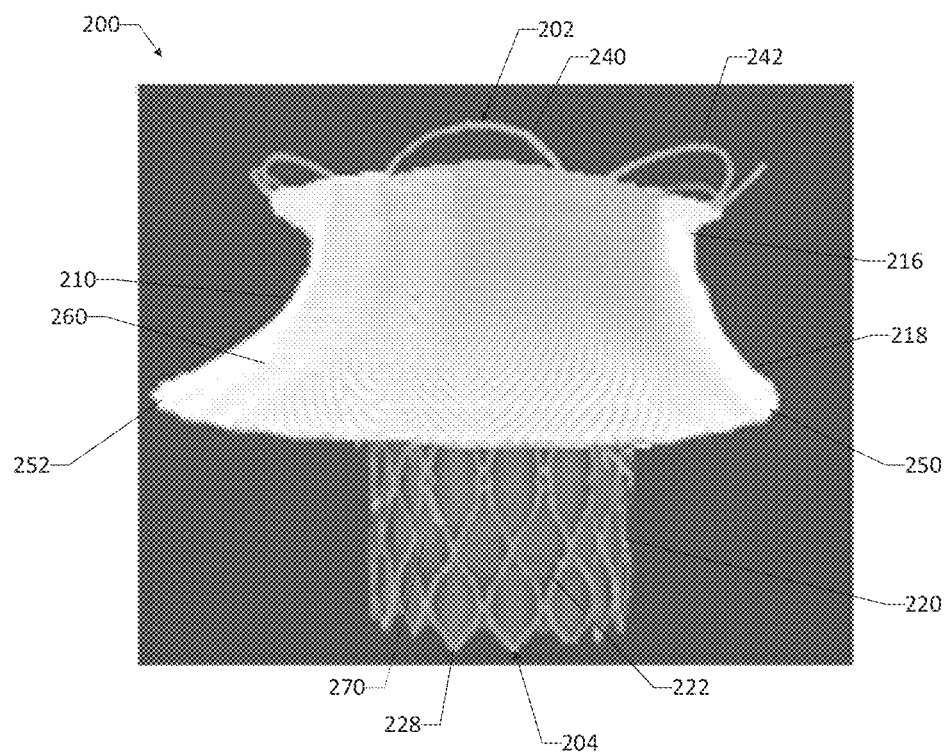
FIG. 2A is a side view of a prosthetic heart valve in accordance with one or more embodiments of the present disclosure, showing the prosthetic heart valve in an expanded state.
Figure 2B:
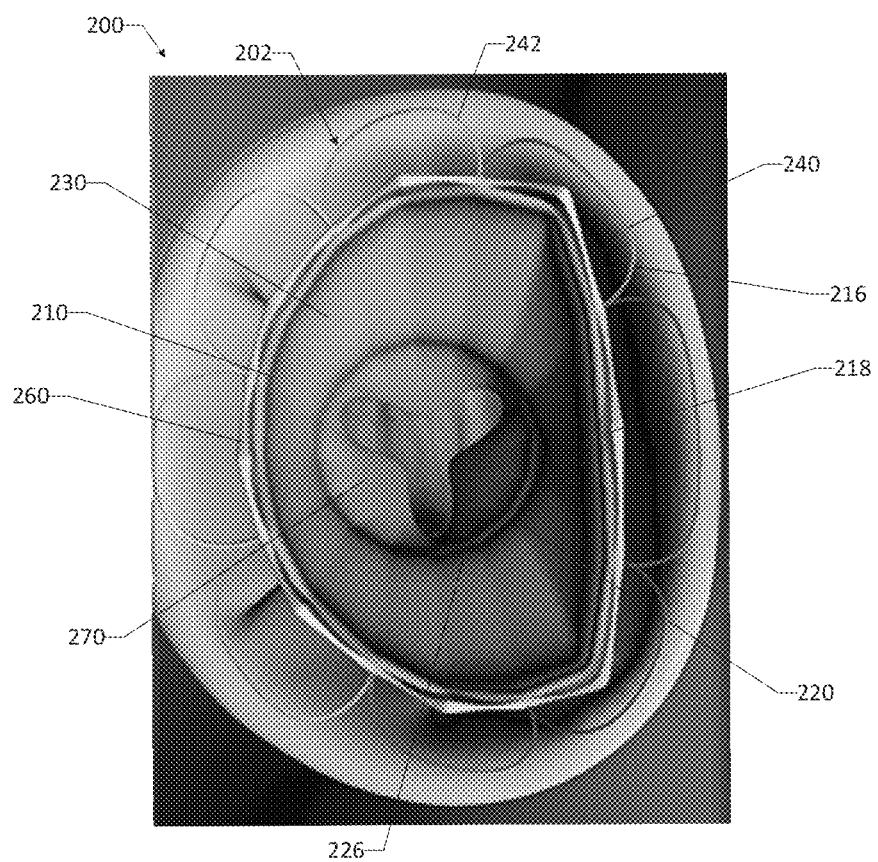
FIG. 2B is a top view of the prosthetic heart valve of FIG. 2A, showing the prosthetic heart valve in the expanded state.
Figure 2C:
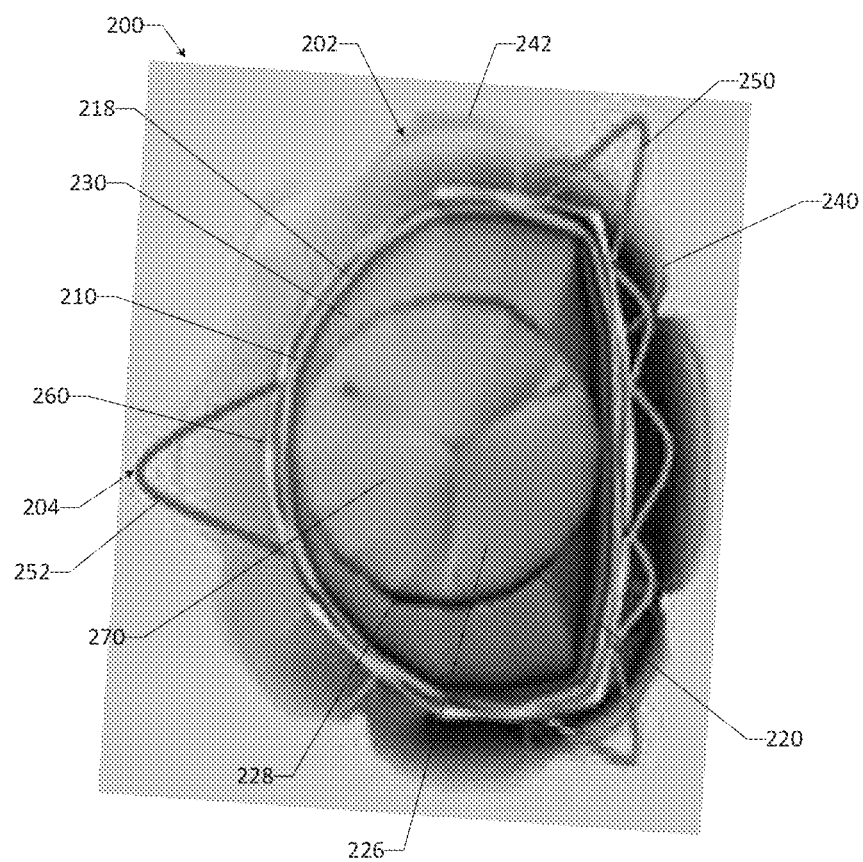
FIG. 2C is a bottom view of the prosthetic heart valve of FIG. 2A, showing the prosthetic heart valve in the expanded state.
Figure 2D:
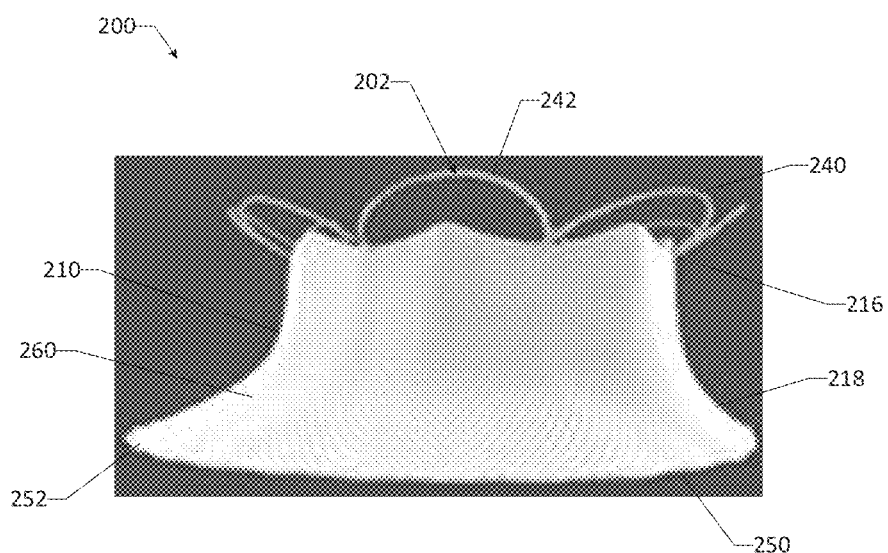
FIG. 2D is a side view of an outer frame, an atrial flange/skirt, and a ventricular flange/skirt of the prosthetic heart valve of FIG. 2A, showing the outer frame, the atrial flange/skirt, and the ventricular flange/skirt in the expanded state.
Figure 2G:
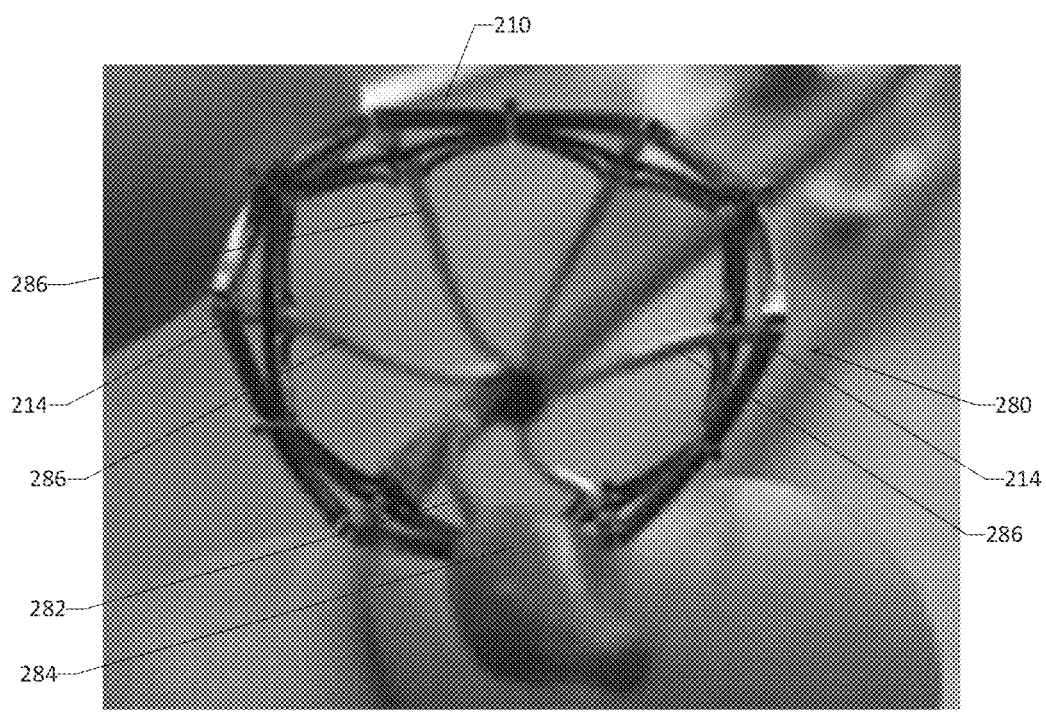
FIG. 2G is a bottom perspective view of the outer frame of the prosthetic heart valve of FIG. 2A and a portion of the delivery device, showing the outer frame in the expanded state.
Figure 2H:
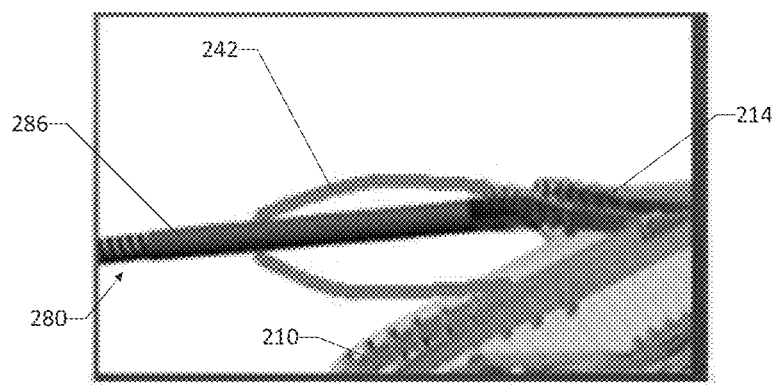
FIG. 2H is a detailed side view of a portion of the prosthetic heart valve of FIG. 2A and a portion of the delivery device, showing a petal of the atrial flange/skirt of the prosthetic heart valve in a collapsed state.
Figure 2I:
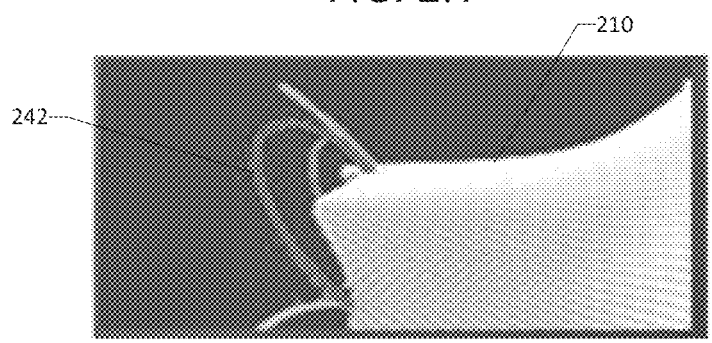
FIG. 2I is a detailed side view of a portion of the prosthetic heart valve of FIG. 2A, showing petals of the atrial flange/skirt in an expanded state.
Figure 2J:
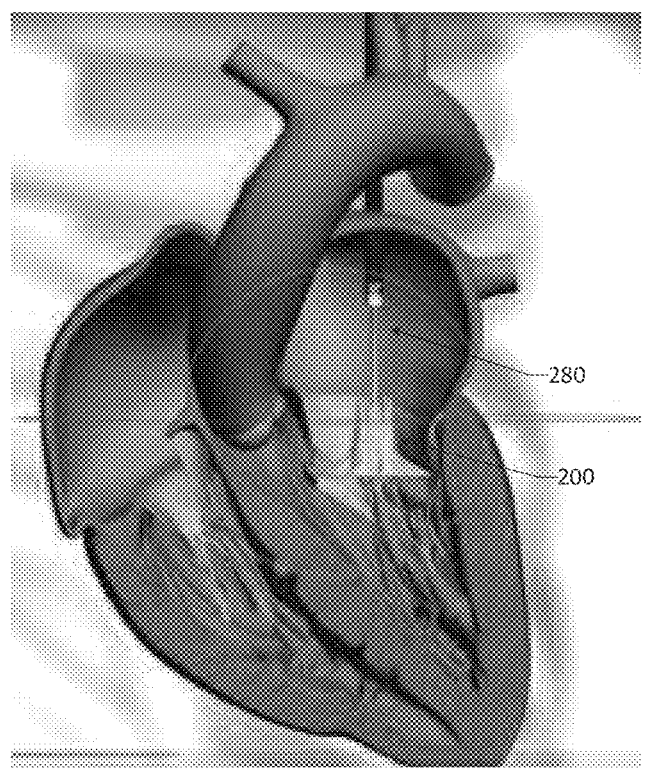
FIG. 2J is a partial cross-sectional side view of the prosthetic heart valve of FIG. 2A positioned within a native mitral valve of a native human heart, showing the outer frame and the atrial flange/skirt of the prosthetic heart valve in a collapsed state and the ventricular flange/skirt in an expanded state.

Various embodiments of the present disclosure provide improved expandable prosthetic heart valves, delivery devices, and methods for replacing diseased or defective native heart valves. Such expandable prosthetic heart valves, delivery devices, and methods may address one or more of the above-described drawbacks of existing technology for heart valve replacement. As described below, the expandable prosthetic heart valves, delivery devices, and methods provided herein may be configured for mitral valve replacement, although the expandable prosthetic heart valves, delivery devices and methods alternatively may be configured for aortic, pulmonary, or tricuspid valve replacement.

Embodiments of the present disclosure are described herein below with reference to the accompanying drawings, in which some, but not all, embodiments are shown. Indeed, the prosthetic heart valves, delivery devices, and methods disclosed may be embodied in many different forms and should not be construed as limited to the embodiments set forth herein; rather, these embodiments are provided so that this disclosure is thorough and complete and fully conveys the scope of the prosthetic heart valves, delivery devices, and methods to those skilled in the art. Like reference numbers refer to like elements throughout. The singular forms "a," "an," and "the" can refer to plural instances unless the context clearly dictates otherwise or unless explicitly stated.

As described in detail below, the embodiments of the present disclosure provide improved prosthetic heart valves, delivery devices, and methods for replacing diseased or defective native heart valves, such as mitral valves, aortic valves, pulmonary valves, or tricuspid valves, of a native human heart. In particular, some embodiments of the prosthetic heart valve may be configured for mitral valve replacement and may be implanted via open heart surgery or less-invasive approaches, such as a transapical approach, a transatrial approach, a transfemoral approach, a transseptal approach, a subclavian approach, a direct aortic puncture approach, or other vascular access approaches. Such embodiments of the prosthetic heart valve may accommodate the shape and structure of the native mitral valve and the surrounding anatomy without compromising the integrity or function of the surrounding anatomy. Such embodiments of the prosthetic heart valve also may securely anchor onto the native heart tissue to prevent or inhibit migration of the prosthetic heart valve from the implantation site. Further, such embodiments of the prosthetic heart valve may form a seal against the native heart tissue to prevent or inhibit paravalvular leakage.

Although the following description focuses primarily on use of the prosthetic heart valve for mitral valve replacement, it will be understood that some embodiments of the prosthetic heart valve may be configured for use in aortic, pulmonary, or tricuspid valve replacement. As will be appreciated by one of ordinary skill in the art, development of a prosthetic heart valve for replacement of the native mitral valve may present numerous technical and clinical challenges which must be taken in to account in order to provide a suitable prosthetic heart valve for mitral, aortic, pulmonary, or tricuspid valve replacement. For example, technical challenges and considerations include, but are not limited to, implanting the prosthetic heart valve at a narrow landing site on the native heart with limited imaging of the native heart anatomy and the prosthetic heart valve during implantation, navigating and accommodating the three-dimensional, dynamic native heart anatomy and complex sub-valvular features, accommodating the pressure gradient at the desired implantation site and the annular loads applied to the prosthetic heart valve by the native heart anatomy, providing adequate sealing against the native heart anatomy to prevent or inhibit paravalvular leakage, gaining access to the desired implantation site and guiding a relatively large prosthetic heart valve through the vasculature to the implantation site, avoiding undesirable thrombosis that may inhibit desired function of the prosthetic heart valve and/or surrounding features of the native heart, avoiding left ventricular outflow tract obstruction (LVOTO), and avoiding systolic anterior motion (SAM) of the mitral valve chordae tendinae. Clinical challenges and considerations include, but are not limited to, accommodating the particular complications of the sick population in need of valve replacement, identifying and addressing multiple and very different etiologies, such as ischemic, dilated cardiomyopathy, degenerative, and rheumatic etiologies, addressing an increased international normalized ratio (INR) because of thrombus potential including gastro-intestinal and other bleeds, and addressing atrial fibrillation.

According to one aspect, a prosthetic heart valve for replacing a diseased or defective native heart valve is provided. In one embodiment, the prosthetic heart valve may include an outer frame, an inner frame positioned at least partially within the outer frame, and an occluder member positioned at least partially within the inner frame. The prosthetic heart valve also may include an atrial flange extending from an atrial end of the outer frame, and a ventricular flange extending from a ventricular end of the outer frame, wherein at least a portion of the atrial flange extends radially outward beyond the ventricular flange.

In another embodiment, the prosthetic heart valve may include an outer frame having a D-shaped cross-sectional shape in a plane orthogonal to a longitudinal axis of the prosthetic heart valve, and an inner frame positioned at least partially within the outer frame and having a circular cross-sectional shape in the plane orthogonal to the longitudinal axis of the prosthetic heart valve. The prosthetic heart valve also may include an occluder member positioned at least partially within the inner frame, an atrial flange extending from an atrial end of the outer frame, and a ventricular flange extending form a ventricular end of the outer frame.

In still another embodiment, the prosthetic heart valve may include an expandable outer frame having a D-shaped cross-sectional shape in a plane orthogonal to a longitudinal axis of the prosthetic heart valve, and an expandable inner frame positioned at least partially within the outer frame and having a circular cross-sectional shape in the plane orthogonal to the longitudinal axis of the prosthetic heart valve. The prosthetic heart valve also may include an occluder member positioned at least partially within the inner frame, an atrial flange extending from an atrial end of the outer frame, and a ventricular flange extending from a ventricular end of the outer frame, wherein at least a portion of the atrial flange extends radially outward beyond the ventricular flange.

Various aspects of the prosthetic heart valves, delivery devices, and methods described herein build upon those described in the following patent applications, which are incorporated by reference herein, in their entirety, for all purposes: U.S. application Ser. No. 11/888,009, filed Jul. 31, 2007; U.S. application Ser. No. 12/822,291, filed Jun. 24, 2010; U.S. application Ser. No. 13/339,236, filed Dec. 28, 2011; U.S. application Ser. No. 13/656,717, filed Oct. 21, 2012; U.S. application Ser. No. 13/772,203, filed Feb. 20, 2013; U.S. application Ser. No. 14/208,997, filed Mar. 13, 2014; U.S. application Ser. No. 14/278,594, filed May 15, 2014; PCT Application No. PCT/US2007/017061, filed Jul. 31, 2007; PCT Application No. PCT/US2011/067695, filed Dec. 29, 2011; PCT Application No. PCT/US2012/061292, filed Oct. 22, 2012; PCT Application No. PCT/US2013/027072, filed Feb. 21, 2013; and PCT Application No. PCT/US2014/038305, filed May 16, 2014. As will be appreciated by one of ordinary skill in the art, various features of the prosthetic heart valves, delivery devices, and methods described herein may be incorporated into the prosthetic heart valves, delivery devices, and methods described in the foregoing applications, and various features of the prosthetic heart valves, delivery devices, and methods described in the foregoing applications may be incorporated into the prosthetic heart valves, delivery devices, and methods described herein.

Referring now to the drawings, FIGS. 1A-1F illustrate an expandable prosthetic heart valve 100 (which also may be referred to as a "heart valve" or a "heart valve device") according to one or more embodiments of the disclosure. In some embodiments, the prosthetic heart valve 100 may be configured for implantation at a diseased or defective native mitral valve of a human heart to replace the function of the native mitral valve. In other embodiments, the prosthetic heart valve 100 may be configured for implantation at a diseased or defective native aortic valve, pulmonary valve, or tricuspid valve of a human heart to replace the function of the native valve. As described below, the prosthetic heart valve 100 may accommodate the shape and structure of the native mitral valve and the surrounding anatomy without compromising the integrity or function of the surrounding anatomy, may securely anchor onto the native heart tissue to prevent or inhibit migration of the prosthetic heart valve 100 from the implantation site, and may form a seal against the native heart tissue to prevent or inhibit paravalvular leakage. Ultimately, the prosthetic heart valve 100 may restore desired function of the native heart by controlling blood flow in a manner similar to the native mitral valve being replaced.

The prosthetic heart valve 100 may be formed as a generally tubular structure having an elongated shape extending along a longitudinal axis of the heart valve 100. The prosthetic heart valve 100 may be implanted within the native mitral valve such that the longitudinal axis of the prosthetic heart valve 100 is generally aligned with the longitudinal axis of the native mitral valve. When positioned at the desired implantation site, an end portion of the heart valve 100 may be positioned within the left atrium of the heart, another end portion of the heart valve 100 may be positioned within the left ventricle of the heart, and an intermediate portion of the heart valve 100 may be positioned within the annulus of the native mitral valve. In this manner, the prosthetic heart valve 100 may have an atrial end 102 (which also may be referred to as a "proximal end" or a "first end") and an ventricular end 104 (which also may be referred to as a "distal end" or a "second end") positioned opposite the atrial end 102 along the longitudinal axis of the heart valve 100. As described below, the prosthetic heart valve 100 may be expandable, such that the heart valve 100 may be moved between a collapsed state for delivery of the heart valve 100 to the desired implantation site and an expanded state for anchoring the heart valve 100 to the heart at the implantation site. In particular, the prosthetic heart valve 100 maybe configured for controlled expansion into one of a number of expanded states, such that the heart valve 100 may be expanded to an expanded state that corresponds to the size and shape of the anatomy of a particular patient. The prosthetic heart valve 100 also may be configured for controlled contraction from an expanded state toward or to the collapsed state, such that the heart valve 100 may be at least partially collapsed in order to reposition the heart valve 100 with respect to the heart anatomy, if necessary. In this manner, the prosthetic heart valve 100 may provide significant advantages over existing heart valves that are either self-expanding or are expanded by a balloon or other mechanism and do not provide a means for easily contracting or repositioning the heart valve.

The prosthetic heart valve 100 may include an outer frame 110 (which also may be referred to as a "radially outer frame") and an inner frame 120 (which also may be referred to as a "radially inner frame") positioned at least partially within the outer frame 110. The outer frame 110 may be a generally tubular structure having an elongated shape extending along the longitudinal axis of the heart valve 100. The outer frame 110 may be formed as a lattice or stent-like structure that radially expands and collapses as the prosthetic heart valve 100 is moved between the collapsed state and the expanded state. As shown, the lattice of the outer frame 110 may include a number of interconnected wire members 112 configured to deflect and/or articulate as the prosthetic heart valve 100 is moved between the collapsed state and the expanded state. The lattice of the outer frame 110 may be formed of a metal wire, although other materials and configurations of the lattice may be used. In some embodiments, the outer frame 110 may be formed of a shape memory alloy, such as nitinol, or a shape memory polymer, although other suitable metals, alloys, and polymers may be used. The lattice of the outer frame 110 may be configured such that controlled changes in the axial dimensions of the wire members 112 results in controlled changes to the orthogonal dimensions or diameter of the outer frame 110. Changes to the dimensions of the lattice of the outer frame 110 may be prescribed by mechanical interaction between the wire members 112 and other mechanical elements, such as screws or rods, which may define different positions for specific points in the lattice and, in doing so, may define an axial length of the lattice and thus its resulting diameter. For example, the outer frame 110 may include a number of actuator members 114 configured to facilitate movement of the prosthetic heart valve 100 between the collapsed state and the expanded state. In some embodiments, as shown, the actuator members 114 may include a threaded rod received within a threaded tube. The actuator members 114 may be attached to a number of the wire members 112, thereby forming a screw-jack mechanism to facilitate movement of the prosthetic heart valve 100 between the collapsed state and the expanded state. In other embodiments, the actuator members 114 may have other configurations for separately articulating the wire members 112 and selectively moving all or a portion of the prosthetic heart valve 100 between the collapsed state and the expanded state. In some embodiments, the actuator elements are rods that have multiple points that generate mechanical interference with a selective locking element at different states of expansion or contraction. The outer frame 110 may have a longitudinal axis which may be coaxial with or spaced apart from the longitudinal axis of the prosthetic heart valve 100. The outer frame 110 may have an atrial end 116 (which also may be referred to as a "proximal end" or a "first end"), and a ventricular end 118 (which also may be referred to as a "distal end" or a "second end") positioned opposite the atrial end 116 along the longitudinal axis of the outer frame 110.

The inner frame 120 may be a generally tubular structure having an elongated shape extending along the longitudinal axis of the heart valve 100. The inner frame 120 also may be formed as a lattice or stent-like structure that radially expands and collapses as the prosthetic heart valve 100 is moved between the collapsed state and the expanded state. As shown, the lattice of the inner frame 120 may include a number of interconnected wire members 122 configured to deflect and/or articulate as the prosthetic heart valve 100 is moved between the collapsed state and the expanded state. The lattice of the inner frame 120 may be formed of a deformable metal wire, although other materials and configurations of the lattice may be used. In some embodiments, the inner frame 120 may be formed of a shape memory alloy, such as nitinol, or a shape memory polymer, although other suitable metals, alloys, and polymers may be used. although other suitable The inner frame 120 may have a longitudinal axis which may be coaxial with or spaced apart from the longitudinal axis of the prosthetic heart valve 100 and which may be coaxial with or spaced apart from the longitudinal axis of the outer frame 110. The inner frame 120 may have an atrial end 126 (which also may be referred to as a "proximal end" or a "first end"), and a ventricular end 128 (which also may be referred to as a "distal end" or a "second end") positioned opposite the atrial end 126 along the longitudinal axis of the inner frame 120. As shown, the atrial end 126 of the inner frame 120 may be positioned within the lumen of the outer frame 110, and the ventricular end 128 of the inner frame 120 may be positioned outside of the lumen of the outer frame 110. In some embodiments, as shown, the ventricular end 128 of the inner frame 120 may be positioned at the ventricular end 104 of the prosthetic heart valve 100.

The outer frame 110 and the inner frame 120 may have a variety of cross-sectional shapes in a plane orthogonal to the longitudinal axes thereof. In various embodiments, the outer frame 110 may have a circular shape, an elliptical shape, a "D"-shape, a square shape, a rectangular shape, a polygonal shape, a curved shape, or a shape having one or more curved sections and one or more straight sections in the plane orthogonal to the longitudinal axis of the outer frame 110. In some embodiments, the cross-sectional shape of the outer frame 110 may be constant along the longitudinal direction. In other embodiments, the cross-sectional shape of the outer frame 110 may vary along the longitudinal direction. In some embodiments, the size of the cross-sectional shape of the outer frame 110 may be constant along the longitudinal direction. In other embodiments, the size of the cross-sectional shape of the outer frame 110 may vary along the longitudinal direction. In various embodiments, the inner frame 120 may have a circular shape, an elliptical shape, a "D"-shape, a square shape, a rectangular shape, a polygonal shape, a curved shape, or a shape having one or more curved sections and one or more straight sections in the plane orthogonal to the longitudinal axis of the inner frame 120. In some embodiments, the cross-sectional shape of the inner frame 120 may be constant along the longitudinal direction. In other embodiments, the cross-sectional shape of the inner frame 120 may vary along the longitudinal direction. In some embodiments, the size of the cross-sectional shape of the inner frame 120 may be constant along the longitudinal direction. In other embodiments, the size of the cross-sectional shape of the inner frame 120 may vary along the longitudinal direction. In some embodiments, the outer frame 110 may have a "D"-shape and the inner frame 120 may have a circular shape. In this manner, the outer frame 110 may be shaped to accommodate the generally "D"-shape of the native mitral valve, while the inner frame 120 may be shaped to accommodate an occluder member, such as a multi-leaflet valve, having a generally circular shape. Notably, use of the "D"-shaped outer frame 110 may reduce the possibility of left ventricular outflow tract obstruction. In other embodiments, the outer frame 110 may have a circular shape and the inner frame 120 may have a circular shape. In still other embodiments, the outer frame 110 and the inner frame 120 may have other shapes, which may be the same as or different from one another. In some embodiments, the outer frame 110 and the inner frame 120 may have the same longitudinal heights, although different longitudinal heights of the outer frame 110 and the inner frame 120 may be used in other embodiments.

As shown, the outer frame 110 and the inner frame 120 may be connected to one another by a trampoline 130 (which also may be referred to as an "intermediate frame" or an "intermediate support") that extends radially between the outer frame 110 and the inner frame 120. In this manner, the trampoline 130 may maintain a relative position of the inner frame 120 with respect to the outer frame 110 and may guide the inner frame 120 during expansion and contraction of the prosthetic heart valve 100. In particular, the trampoline 130 may transfer forces from the outer frame 110 to the inner frame 120 as the outer frame 110 is expanded or collapsed, thereby causing the inner frame 120 to expand or collapse in a similar manner. As shown, the trampoline 130 may be formed as a lattice including a number of interconnected wire members 132 configured to deflect and/or articulate as the prosthetic heart valve 100 is moved between the collapsed state and the expanded state. The trampoline 130 may provide a contoured transition between the outer frame 110 and the inner frame 120, particularly when the outer frame 110 and the inner frame 120 have different cross-sectional shapes. In some embodiments, the trampoline 130 may be attached to the outer frame 110 and the inner frame 120 by mechanical fasteners, welding, soldering, bonding, chemical bonding or attachment, or other suitable means of attachment. In other embodiments, the outer frame 110, the inner frame 120, and the trampoline 130 may be formed from a single piece of material, which may be bent to form the respective shapes of the outer frame 110, the inner frame 120, and the trampoline 130.

As shown, the prosthetic heart valve 100 also may include a pair of flanges attached to the outer frame 110. In particular, the prosthetic heart valve 100 may include an atrial flange 140 (which also may be referred to as an "atrial skirt," a "proximal flange," a "proximal skirt," or an "extended sealing surface") attached to the atrial end 116 of the outer frame 110 and extending axially and/or radially outward therefrom. In some embodiments, the atrial flange 140 may be spaced apart from and positioned along the outer surface of the outer frame 110 distally from the atrial end 116 of the outer frame 110. During implantation of the prosthetic heart valve 100, the atrial flange 140 may be positioned within the left atrium of the heart and in apposition against a tissue surface therein above the mitral valve annulus. The atrial flange 140 may be flexible such that the atrial flange 140 may be collapsed and expanded along with the outer frame 110 to facilitate positioning and anchoring of the outer frame 110 at the implantation site. As shown, the atrial flange 140 may include a number of petals 142 positioned in a circumferential array along the circumference of the outer frame 110. The petals 142 may be formed of a metal or polymer wire, although other materials and configurations of the petals 142 may be used. In some embodiments, the petals 142 may be formed of wire mesh or stent lattice.

The prosthetic heart valve 100 also may include a ventricular flange 150 (which also may be referred to as a "ventricular skirt," a "distal flange," a "distal skirt," or an "extended sealing surface") attached to the ventricular end 118 of the outer frame 110 and extending axially and radially outward therefrom. In some embodiments, the ventricular flange 150 may be spaced apart from and positioned along the outer surface of the outer frame 110 proximally from the ventricular end 118 of the outer frame 110. During implantation of the prosthetic heart valve 100, the ventricular flange 150 may be positioned within the left ventricle of the heart and in apposition against a tissue surface therein below the mitral valve annulus. The ventricular flange 150 may be flexible such that the ventricular flange 150 may be collapsed and expanded along with the outer frame 110 to facilitate positioning and anchoring of the outer frame 110 at the implantation site. As shown, the ventricular flange 150 may include a number of petals 152 positioned in a circumferential array along the circumference of the outer frame 110. The petals 152 may be formed of a metal or polymer wire, although other materials and configurations of the petals 152 may be used. In some embodiments, the petals 152 may be formed of wire mesh or stent lattice.

Notably, the atrial flange 140 and the ventricular flange 150 may facilitate mechanical interference based anchoring of the prosthetic heart valve 100 onto the heart as well as pressure-driven sealing between the heart valve 100 and the mating heart tissue. Such anchoring and sealing benefits may be particularly advantageous in mitral valve replacement because the presence of the left ventricular outflow tract, the more compliant tissue, the shorter annuli, and the increased area of dilated annuli do not allow for reliance only on radial force for sealing and anchoring, as in aortic valve replacement. In some embodiments, the ventricular flange 150 may be larger than the atrial flange 140, such that the ventricular flange 150 has a larger cross-sectional area than the atrial flange 140 in the plane orthogonal to the longitudinal axis of the. In some embodiments, at least a portion of the ventricular flange 150 may extend radially outward beyond the atrial flange 140. In other embodiments, the ventricular flange 150 may extend radially outward beyond the atrial flange 140 along the entire circumference of the flanges 140, 150. In some embodiments, all of the petals 142 of the atrial flange 140 may have the same size, with the same axial length and the same radial length. In other embodiments, the petals 142 of the atrial flange 140 may vary in their axial length and/or their radial length along the circumference of the atrial flange 140. In some embodiments, one or more of the petals 142 configured to be positioned at or near the trigones of the mitral valve may be stiffer and/or longer that a remainder of the petals 142. In this manner, such embodiments may provide enhanced anchoring about the trigones of the mitral valve. In some embodiments, all of the petals 152 of the ventricular flange 150 may have the same size, with the same axial length and the same radial length. In other embodiments, the petals 152 of the ventricular flange 150 may vary in their axial length and/or their radial length along the circumference of the ventricular flange 150. In some embodiments, one or more of the petals 152 configured to be positioned at or near the trigones of the mitral valve may be stiffer and/or longer that a remainder of the petals 152. In this manner, such embodiments may provide enhanced anchoring about the trigones of the mitral valve.

As shown, the prosthetic heart valve 100 may include a biocompatible covering 160 (which also may be referred to as a "membrane") positioned over portions of the outer frame 110, the inner frame 120, the trampoline 130, the atrial flange 140, and/or the ventricular flange 150. The outer frame 110, the inner frame 120, the trampoline 130, the atrial flange 140, and/or the ventricular flange 150 each may be partially or entirely covered by the covering 160, according to various embodiments. The covering 160 may be formed as a single component positioned over the respective portions of the heart valve 100 or as multiple components positioned over the respective portions of the heart valve 100. In some embodiments, the covering 160 extends over the outer surfaces and/or the inner surfaces of the outer frame 110, the inner frame 120, the trampoline 130, the atrial flange 140, and/or the ventricular flange 150. In some embodiments, the covering 160 is formed of a biocompatible cloth or textile material, although other suitable materials may be used for the covering 160. When the prosthetic heart valve 100 is implanted, the covering 160 may promote hemostasis at the implantation site, preventing or inhibiting blood flow around the heart valve 100. The covering 160 also may promote tissue ingrowth or overgrowth to facilitate anchoring of the prosthetic heart valve 100 to the heart tissue.

The prosthetic heart valve 100 further may include an occluder member 170 (which also may be referred to simply as an "occluder") attached to the inner frame 120 and positioned at least partially within the lumen thereof. The occluder member 170 may be configured to control blood blow through the prosthetic heart valve 100 in a manner similar to the native heart valve being replaced. In some embodiments, as shown, the occluder member 170 may be a multi-leaflet valve including a number of leaflets 172 arranged to form a one-way valve to control blood flow therebetween. The leaflets 172 may be formed of a metal, a polymer, a ceramic, a composite material, or a bioprosthetic material. For example, the leaflets 172 may be bioprosthetic leaflets of treated animal tissue, such as porcine, bovine, or equine tissue. In other embodiments, the occluder member 170 may include one or more spheres, one or more discs, one or more rotating plates, or other types of members configured to control blood flow. Any such embodiments may be configured as a one-directional occluder member, allowing blood flow therethrough in one direction and preventing blood flow in an opposite direction.

In some embodiments, the prosthetic heart valve 100 also may include one or more anchors attached to the outer frame 110 and extending radially outward therefrom. During implantation of the prosthetic heart valve 100, the anchors may be configured to pierce or create a mechanical interference with the surrounding heart tissue, such as the native mitral valve annulus. In this manner, the anchors may further secure the position of the prosthetic heart valve 100 at the implantation site. In some embodiments, the anchors may be fixed relative to the outer frame 110 and may engage the surrounding heart tissue as the prosthetic heart valve 100 is expanded within the native mitral valve. In other embodiments, the anchors may be deployed from a retracted state for positioning of the prosthetic heart valve 100 to a deployed state for engaging the surrounding heart tissue. In some embodiments, the anchors may be formed as prongs or hooks, although other configurations of the anchors may be used.

The prosthetic heart valve 100 may be delivered to the desired implantation site and anchored to the native heart via a delivery device 180. As shown, the delivery device 180 may include a shaft 182 with a guide tip 184 attached to a distal end of the shaft 182. During use of the delivery device 180, the guide tip 184 and a distal portion of the shaft 182 may extend through the prosthetic heart valve 100, as shown, to guide the prosthetic heart valve 100 through the vasculature to the implantation site. The delivery device 180 also may include a sheath positioned over the shaft 182 and configured to retain the prosthetic heart valve 100 in the collapsed state therein until the distal end portion of the delivery device 180 reaches the implantation site. The sheath then may be retracted to expose the prosthetic heart valve 100. The delivery device 180 also may include a number of control wires 186 configured to attach to the actuator members 114 of the outer frame 110. In some embodiments, the control wires 186 may be threaded and configured to threadably attach to the actuator members 114, although other means of attachment may be used. After the prosthetic heart valve 100 is exposed and positioned within the native mitral valve, the control wires 186 may be manipulated to actuate the actuator members 114, thereby causing the outer frame 110 to controllably expand from the collapsed state. As described above, expansion of the outer frame 110 also may cause the inner frame 120 to expand. The prosthetic heart valve 100 may be expanded in this manner within the native mitral valve until the outer surface of the outer frame 110 sufficiently engages the native mitral valve annulus to maintain a relative position of the prosthetic heart valve 100 with respect to the native mitral valve. Upon such expansion, the anchors, if present, may engage the mitral valve annulus or other heart tissue. Meanwhile, the ventricular flange 150 may expand within the left ventricle of the heart and engage the tissue surface below the mitral valve annulus. Once the desired positioning of the prosthetic heart valve 100 within the native mitral valve is obtained, the control wires 186 may be disengaged from the actuator members 114. Upon disengaging the control wires 186, the atrial flange 140 may expand within the left atrium and engage the tissue surface above the mitral valve annulus. Ultimately, the engagement between the outer frame 110 and the mitral valve annulus, the engagement between the ventricular flange 150 and the mating tissue surface, and the engagement between the atrial flange 140 and the mating tissue surface may securely anchor the prosthetic heart valve 100 within the native mitral valve. In embodiments that include the anchors, the engagement between the anchors and the mating tissue may further anchor the prosthetic heart valve 100. Meanwhile, the engagement between the covering 160 and the mating tissue surfaces, the engagement between the ventricular flange 150 and the mating tissue surface, and the engagement between the atrial flange 140 and the mating tissue surface may provide one or more seals that prevent or inhibit blood flow around the prosthetic heart valve 100 and also may promote tissue ingrowth or overgrowth to further seal and anchor the prosthetic heart valve 100. The prosthetic heart valve 100 described herein may be configured for anchoring onto a mitral valve annulus having a commissural diameter in the range of between 2 cm and 7 cm, which may cover a majority of patients in need of heart valve replacement.

FIGS. 2A-2J illustrate an expandable prosthetic heart valve 200 (which also may be referred to as a "heart valve" or a "heart valve device") according to one or more embodiments of the disclosure. In some embodiments, the prosthetic heart valve 200 may be configured for implantation at a diseased or defective native mitral valve of a human heart to replace the function of the native mitral valve. In other embodiments, the prosthetic heart valve 200 may be configured for implantation at a diseased or defective native aortic valve, pulmonary valve, or tricuspid valve of a human heart to replace the function of the native valve. As described below, the prosthetic heart valve 200 may accommodate the shape and structure of the native mitral valve and the surrounding anatomy without compromising the integrity or function of the surrounding anatomy, may securely anchor onto the native heart tissue to prevent or inhibit migration of the prosthetic heart valve 200 from the implantation site, and may form a seal against the native heart tissue to prevent or inhibit paravalvular leakage. Ultimately, the prosthetic heart valve 200 may restore desired function of the native heart by controlling blood flow in a manner similar to the native mitral valve being replaced.

The prosthetic heart valve 200 may be formed as a generally tubular structure having an elongated shape extending along a longitudinal axis of the heart valve 200. The prosthetic heart valve 200 may be implanted within the native mitral valve such that the longitudinal axis of the prosthetic heart valve 200 is generally aligned with the longitudinal axis of the native mitral valve. When positioned at the desired implantation site, an end portion of the heart valve 200 may be positioned within the left atrium of the heart, another end portion of the heart valve 200 may be positioned within the left ventricle of the heart, and an intermediate portion of the heart valve 200 may be positioned within the annulus of the native mitral valve. In this manner, the prosthetic heart valve 200 may have an atrial end 202 (which also may be referred to as a "proximal end" or a "first end") and an ventricular end 204 (which also may be referred to as a "distal end" or a "second end") positioned opposite the atrial end 202 along the longitudinal axis of the heart valve 200. As described below, the prosthetic heart valve 200 may be expandable, such that the heart valve 200 may be moved between a collapsed state for delivery of the heart valve 200 to the desired implantation site and an expanded state for anchoring the heart valve 200 to the heart at the implantation site. In particular, the prosthetic heart valve 200 may be configured for controlled expansion into one of a number of expanded states, such that the heart valve 200 may be expanded to an expanded state that corresponds to the size and shape of the anatomy of a particular patient. The prosthetic heart valve 200 also may be configured for controlled contraction from an expanded state toward or to the collapsed state, such that the heart valve 200 may be at least partially collapsed in order to reposition the heart valve 200 with respect to the heart anatomy, if necessary. In this manner, the prosthetic heart valve 200 may provide significant advantages over existing heart valves that are either self-expanding or are expanded by a balloon or other mechanism and do not provide a means for easily contracting or repositioning the heart valve.

The prosthetic heart valve 200 may include an outer frame 210 (which also may be referred to as a "radially outer frame") and an inner frame 220 (which also may be referred to as a "radially inner frame") positioned at least partially within the outer frame 210. The outer frame 210 may be a generally tubular structure having an elongated shape extending along the longitudinal axis of the heart valve 200.

The outer frame 210 may be formed as a lattice or stent-like structure that radially expands and collapses as the prosthetic heart valve 200 is moved between the collapsed state and the expanded state. As shown, the lattice of the outer frame 210 may include a number of interconnected wire members 212 configured to deflect and/or articulate as the prosthetic heart valve 200 is moved between the collapsed state and the expanded state. The lattice of the outer frame 210 may be formed of a metal wire, although other materials and configurations of the lattice may be used. In some embodiments, the outer frame 210 may be formed of a shape memory alloy, such as nitinol, or a shape memory polymer, although other suitable metals, alloys, and polymers may be used. The lattice of the outer frame 210 may be configured such that controlled changes in the axial dimensions of the wire members 212 results in controlled changes to the orthogonal dimensions or diameter of the outer frame 210. Changes to the dimensions of the lattice of the outer frame 210 may be prescribed by mechanical interaction between the wire members 212 and other mechanical elements, such as screws or rods, which may define different positions for specific points in the lattice and, in doing so, may define an axial length of the lattice and thus its resulting diameter. For example, the outer frame 210 may include a number of actuator members 214 configured to facilitate movement of the prosthetic heart valve 200 between the collapsed state and the expanded state. In some embodiments, as shown, the actuator members 214 may include a threaded rod received within a threaded tube. The actuator members 214 may be attached to a number of the wire members 212, thereby forming a screw-jack mechanism to facilitate movement of the prosthetic heart valve 200 between the collapsed state and the expanded state. In other embodiments, the actuator members 214 may have other configurations for articulating the wire members 212 and moving the prosthetic heart valve 200 between the collapsed state and the expanded state. The outer frame 210 may have a longitudinal axis which may be coaxial with or spaced apart from the longitudinal axis of the prosthetic heart valve 200. The outer frame 210 may have an atrial end 216 (which also may be referred to as a "proximal end" or a "first end"), and a ventricular end 218 (which also may be referred to as a "distal end" or a "second end") positioned opposite the atrial end 216 along the longitudinal axis of the outer frame 210.

The inner frame 220 may be a generally tubular structure having an elongated shape extending along the longitudinal axis of the heart valve 200. The inner frame 220 also may be formed as a lattice or stent-like structure that radially expands and collapses as the prosthetic heart valve 200 is moved between the collapsed state and the expanded state. As shown, the lattice of the inner frame 220 may include a number of interconnected wire members 222 configured to deflect and/or articulate as the prosthetic heart valve 200 is moved between the collapsed state and the expanded state. The lattice of the inner frame 220 may be formed of a deformable metal wire, although other materials and configurations of the lattice may be used. In some embodiments, the inner frame 220 may be formed of a shape memory alloy, such as nitinol, or a shape memory polymer, although other suitable metals, alloys, and polymers may be used. although other suitable The inner frame 220 may have a longitudinal axis which may be coaxial with or spaced apart from the longitudinal axis of the prosthetic heart valve 200 and which may be coaxial with or spaced apart from the longitudinal axis of the outer frame 210. The inner frame 220 may have an atrial end 226 (which also may be referred to as a "proximal end" or a "first end"), and a ventricular end 228 (which also may be referred to as a "distal end" or a "second end") positioned opposite the atrial end 226 along the longitudinal axis of the inner frame 220. As shown, the atrial end 226 of the inner frame 220 may be positioned within the lumen of the outer frame 210, and the ventricular end 228 of the inner frame 220 may be positioned outside of the lumen of the outer frame 210. In some embodiments, as shown, the ventricular end 228 of the inner frame 220 may be positioned at the ventricular end 204 of the prosthetic heart valve 200.

The outer frame 210 and the inner frame 220 may have a variety of cross-sectional shapes in a plane orthogonal to the longitudinal axes thereof. In various embodiments, the outer frame 210 may have a circular shape, an elliptical shape, a "D"-shape, a square shape, a rectangular shape, a polygonal shape, a curved shape, or a shape having one or more curved sections and one or more straight sections in the plane orthogonal to the longitudinal axis of the outer frame 210. In some embodiments, the cross-sectional shape of the outer frame 210 may be constant along the longitudinal direction. In other embodiments, the cross-sectional shape of the outer frame 210 may vary along the longitudinal direction. In some embodiments, the size of the cross-sectional shape of the outer frame 210 may be constant along the longitudinal direction. In other embodiments, the size of the cross-sectional shape of the outer frame 210 may vary along the longitudinal direction. In various embodiments, the inner frame 220 may have a circular shape, an elliptical shape, a "D"-shape, a square shape, a rectangular shape, a polygonal shape, a curved shape, or a shape having one or more curved sections and one or more straight sections in the plane orthogonal to the longitudinal axis of the inner frame 220. In some embodiments, the cross-sectional shape of the inner frame 220 may be constant along the longitudinal direction. In other embodiments, the cross-sectional shape of the inner frame 220 may vary along the longitudinal direction. In some embodiments, the size of the cross-sectional shape of the inner frame 220 may be constant along the longitudinal direction. In other embodiments, the size of the cross-sectional shape of the inner frame 220 may vary along the longitudinal direction. In some embodiments, the outer frame 210 may have a "D"-shape and the inner frame 220 may have a circular shape. In this manner, the outer frame 210 may be shaped to accommodate the generally "D"-shape of the native mitral valve, while the inner frame 220 may be shaped to accommodate an occluder member, such as a multi-leaflet valve, having a generally circular shape. Notably, use of the "D"-shaped outer frame 210 may reduce the possibility of left ventricular outflow tract obstruction. In other embodiments, the outer frame 210 may have a circular shape and the inner frame 220 may have a circular shape. In still other embodiments, the outer frame 210 and the inner frame 220 may have other shapes, which may be the same as or different from one another. In some embodiments, the outer frame 210 and the inner frame 220 may have the same longitudinal heights, although different longitudinal heights of the outer frame 210 and the inner frame 220 may be used in other embodiments.

As shown, the outer frame 210 and the inner frame 220 may be connected to one another by a trampoline 230 (which also may be referred to as an "intermediate frame" or an "intermediate support") that extends radially between the outer frame 210 and the inner frame 220. In this manner, the trampoline 230 may maintain a relative position of the inner frame 220 with respect to the outer frame 210 and may guide the inner frame 220 during expansion and contraction of the prosthetic heart valve 200. In particular, the trampoline 230 may transfer forces from the outer frame 210 to the inner frame 220 as the outer frame 210 is expanded or collapsed, thereby causing the inner frame 220 to expand or collapse in a similar manner. As shown, the trampoline 230 may be formed as a lattice including a number of interconnected wire members 232 configured to deflect and/or articulate as the prosthetic heart valve 200 is moved between the collapsed state and the expanded state. The trampoline 230 may provide a contoured transition between the outer frame 210 and the inner frame 220, particularly when the outer frame 210 and the inner frame 220 have different cross-sectional shapes. In some embodiments, the trampoline 230 may be attached to the outer frame 210 and the inner frame 220 by mechanical fasteners, welding, soldering, bonding, chemical bonding or attachment, or other suitable means of attachment. In other embodiments, the outer frame 210, the inner frame 220, and the trampoline 230 may be formed from a single piece of material, which may be bent to form the respective shapes of the outer frame 210, the inner frame 220, and the trampoline 230.

As shown, the prosthetic heart valve 200 also may include a pair of flanges attached to the outer frame 210. In particular, the prosthetic heart valve 200 may include an atrial flange 240 (which also may be referred to as an "atrial skirt," a "proximal flange," a "proximal skirt," or an "extended sealing surface") attached to the atrial end 216 of the outer frame 210 and extending axially and/or radially outward therefrom. In some embodiments, the atrial flange 240 may be spaced apart from and positioned along the outer surface of the outer frame 210 distally from the atrial end 216 of the outer frame 210. During implantation of the prosthetic heart valve 200, the atrial flange 240 may be positioned within the left atrium of the heart and in apposition against a tissue surface therein above the mitral valve annulus. The atrial flange 240 may be flexible such that the atrial flange 240 may be collapsed and expanded along with the outer frame 210 to facilitate positioning and anchoring of the outer frame 210 at the implantation site. As shown, the atrial flange 240 may include a number of petals 242 positioned in a circumferential array along the circumference of the outer frame 210. The petals 242 may be formed of a metal or polymer wire, although other materials and configurations of the petals 242 may be used. In some embodiments, the petals 242 may be formed of wire mesh or stent lattice.

The prosthetic heart valve 200 also may include a ventricular flange 250 (which also may be referred to as a "ventricular skirt," a "distal flange," a "distal skirt," or an "extended sealing surface") attached to the ventricular end 218 of the outer frame 210 and extending axially and radially outward therefrom. In some embodiments, the ventricular flange 250 may be spaced apart from and positioned along the outer surface of the outer frame 210 proximally from the ventricular end 218 of the outer frame 210. During implantation of the prosthetic heart valve 200, the ventricular flange 250 may be positioned within the left ventricle of the heart and in apposition against a tissue surface therein below the mitral valve annulus. The ventricular flange 250 may be flexible such that the ventricular flange 250 may be collapsed and expanded along with the outer frame 210 to facilitate positioning and anchoring of the outer frame 210 at the implantation site. As shown, the ventricular flange 250 may include a number of petals 252 positioned in a circumferential array along the circumference of the outer frame 210. The petals 252 may be formed of a metal or polymer wire, although other materials and configurations of the petals 252 may be used. In some embodiments, the petals 252 may be formed of wire mesh or stent lattice.

Notably, the atrial flange 240 and the ventricular flange 250 may facilitate mechanical interference based anchoring of the prosthetic heart valve 200 onto the heart as well as pressure-driven sealing between the heart valve 200 and the mating heart tissue. Such anchoring and sealing benefits may be particularly advantageous in mitral valve replacement because the presence of the left ventricular outflow tract, the more compliant tissue, the shorter annuli, and the increased area of dilated annuli do not allow for reliance only on radial force for sealing and anchoring, as in aortic valve replacement. In some embodiments, the ventricular flange 250 may be larger than the atrial flange 240, such that the ventricular flange 250 has a larger cross-sectional area than the atrial flange 240 in the plane orthogonal to the longitudinal axis of the. In some embodiments, at least a portion of the ventricular flange 250 may extend radially outward beyond the atrial flange 240. In other embodiments, the ventricular flange 250 may extend radially outward beyond the atrial flange 240 along the entire circumference of the flanges 240, 250. In some embodiments, all of the petals 242 of the atrial flange 240 may have the same size, with the same axial length and the same radial length. In other embodiments, the petals 242 of the atrial flange 240 may vary in their axial length and/or their radial length along the circumference of the atrial flange 240. In some embodiments, one or more of the petals 242 configured to be positioned at or near the trigones of the mitral valve may be stiffer and/or longer that a remainder of the petals 242. In this manner, such embodiments may provide enhanced anchoring about the trigones of the mitral valve. In some embodiments, the petals on the anterior section of the valve which lie between the trigones may be shorter or have another preferential shapes, so as to interfere less with the aortic root. In some embodiments, all of the petals 252 of the ventricular flange 250 may have the same size, with the same axial length and the same radial length. In other embodiments, the petals 252 of the ventricular flange 250 may vary in their axial length and/or their radial length along the circumference of the ventricular flange 250. In some embodiments, one or more of the petals 252 configured to be positioned at or near the trigones of the mitral valve may be stiffer and/or longer that a remainder of the petals 252. In this manner, such embodiments may provide enhanced anchoring about the trigones of the mitral valve. In some embodiments, the petals or any other anchor in the commissural areas in the atrial and/or ventricular sides of the valve, may be configured by location or shape to pass partially or fully between the leaflets, at the commissural edge in order to interfere minimally with leaflet motion.

As shown, the prosthetic heart valve 200 may include a biocompatible covering 260 (which also may be referred to as a "membrane") positioned over portions of the outer frame 210, the inner frame 220, the trampoline 230, the atrial flange 240, and/or the ventricular flange 250. The outer frame 210, the inner frame 220, the trampoline 230, the atrial flange 240, and/or the ventricular flange 250 each may be partially or entirely covered by the covering 260, according to various embodiments. The covering 260 may be formed as a single component positioned over the respective portions of the heart valve 200 or as multiple components positioned over the respective portions of the heart valve 200. In some embodiments, the covering 260 extends over the outer surfaces and/or the inner surfaces of the outer frame 210, the inner frame 220, the trampoline 230, the atrial flange 240, and/or the ventricular flange 250. In some embodiments, the covering 260 is formed of a biocompatible cloth or textile material, although other suitable materials may be used for the covering 260. When the prosthetic heart valve 200 is implanted, the covering 260 may promote hemostasis at the implantation site, preventing or inhibiting blood flow around the heart valve 200. The covering 260 also may promote tissue ingrowth or overgrowth to facilitate anchoring of the prosthetic heart valve 200 to the heart tissue.

The prosthetic heart valve 200 further may include an occluder member 270 (which also may be referred to simply as an "occluder") attached to the inner frame 220 and positioned at least partially within the lumen thereof. The occluder member 270 may be configured to control blood blow through the prosthetic heart valve 200 in a manner similar to the native heart valve being replaced. In some embodiments, as shown, the occluder member 270 may be a multi-leaflet valve including a number of leaflets 272 arranged to form a one-way valve to control blood flow therebetween. The leaflets 272 may be formed of a metal, a polymer, a ceramic, a composite material, or a bioprosthetic material. For example, the leaflets 272 may be bioprosthetic leaflets of treated animal tissue, such as porcine, bovine, or equine tissue. In other embodiments, the occluder member 270 may include one or more spheres, one or more discs, one or more rotating plates, or other types of members configured to control blood flow. Any such embodiments may be configured as a one-directional occluder member, allowing blood flow therethrough in one direction and preventing blood flow in an opposite direction.

In some embodiments, the prosthetic heart valve 200 also may include one or more anchors 274 attached to the outer frame 210 and extending radially outward therefrom. During implantation of the prosthetic heart valve 200, the anchors 274 may be configured to pierce or create a mechanical interference with the surrounding heart tissue, such as the native mitral valve annulus. In this manner, the anchors 274 may further secure the position of the prosthetic heart valve 200 at the implantation site. In some embodiments, the anchors 274 may be fixed relative to the outer frame 210 and may engage the surrounding heart tissue as the prosthetic heart valve 200 is expanded within the native mitral valve. In other embodiments, as shown, the anchors 274 may be deployed from a retracted state for positioning of the prosthetic heart valve 200 to a deployed state for engaging the surrounding heart tissue. In some embodiments, the anchors 274 may be formed as prongs or hooks, although other configurations of the anchors may be used.

The prosthetic heart valve 200 may be delivered to the desired implantation site and anchored to the native heart via a delivery device 280. As shown, the delivery device 280 may include a shaft 282 with a guide tip 284 attached to a distal end of the shaft 282. During use of the delivery device 280, the guide tip 284 and a distal portion of the shaft 282 may extend through the prosthetic heart valve 200, as shown, to guide the prosthetic heart valve 200 through the vasculature to the implantation site. The delivery device 280 also may include a sheath positioned over the shaft 282 and configured to retain the prosthetic heart valve 200 in the collapsed state therein until the distal end portion of the delivery device 280 reaches the implantation site. The sheath then may be retracted to expose the prosthetic heart valve 200. The delivery device 280 also may include a number of control wires 286 configured to attach to the actuator members 214 of the outer frame 210. In some embodiments, the control wires 286 may be threaded and configured to threadably attach to the actuator members 214, although other means of attachment may be used. After the prosthetic heart valve 200 is exposed and positioned within the native mitral valve, the control wires 286 may be manipulated to actuate the actuator members 214, thereby causing the outer frame 210 to controllably expand from the collapsed state. As described above, expansion of the outer frame 210 also may cause the inner frame 220 to expand. The prosthetic heart valve 200 may be expanded in this manner within the native mitral valve until the outer surface of the outer frame 210 sufficiently engages the native mitral valve annulus to maintain a relative position of the prosthetic heart valve 200 with respect to the native mitral valve. Upon such expansion, the anchors 274, if present, may engage the mitral valve annulus or other heart tissue. Meanwhile, the ventricular flange 250 may expand within the left ventricle of the heart and engage the tissue surface below the mitral valve annulus. Once the desired positioning of the prosthetic heart valve 200 within the native mitral valve is obtained, the control wires 286 may be disengaged from the actuator members 214. Upon disengaging the control wires 286, the atrial flange 240 may expand within the left atrium and engage the tissue surface above the mitral valve annulus. Ultimately, the engagement between the outer frame 210 and the mitral valve annulus, the engagement between the ventricular flange 250 and the mating tissue surface, and the engagement between the atrial flange 240 and the mating tissue surface may securely anchor the prosthetic heart valve 200 within the native mitral valve. In embodiments that include the anchors 274, the engagement between the anchors 274 and the mating tissue may further anchor the prosthetic heart valve 200. Meanwhile, the engagement between the covering 260 and the mating tissue surfaces, the engagement between the ventricular flange 250 and the mating tissue surface, and the engagement between the atrial flange 240 and the mating tissue surface may provide one or more seals that prevent or inhibit blood flow around the prosthetic heart valve 200 and also may promote tissue ingrowth or overgrowth to further seal and anchor the prosthetic heart valve 200. The prosthetic heart valve 200 described herein may be configured for anchoring onto a mitral valve annulus having a commissural diameter in the range of between 2 cm and 7 cm, which may cover a majority of patients in need of heart valve replacement.

Figure 3C:
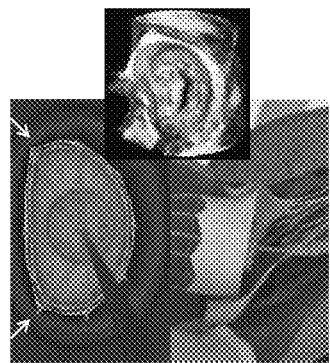
FIG. 3C is a composite top view, a side view and a computer generated positioning top view of the prosthetic heart valve of FIG. 3A showing controlled expansion of the frame, allowing repositioning or re-sheathing by contracting the frame.
Figure 3F:
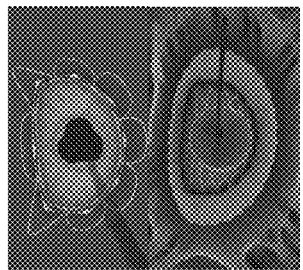
FIG. 3F is a composite top view and a bottom view of the prosthetic heart valve of FIG. 3A showing removing the guide wire and final verification of the valve position and function.
Figure 3B:
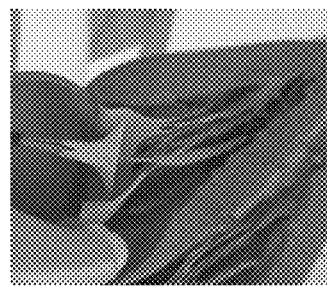
FIG. 3B is a side view of the prosthetic heart valve of FIG. 3A showing unsheathing of the ventricular skirt.
Figure 3E:
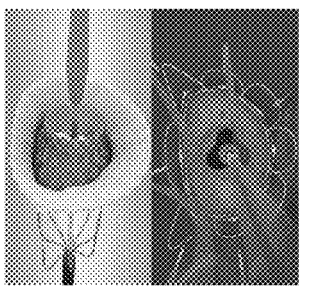
FIG. 3E is a composite of a top perspective view and a top view of the prosthetic heart valve of FIG. 3A showing release of the control wires in the final position.
Figure 3A:
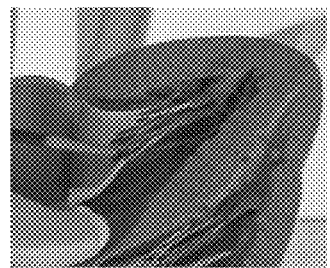
FIG. 3A is a side view of a sheathed prosthetic heart valve, beginning a series in FIGS. 3A-3F showing a computer-assisted mitral valve replacement of the invention.
Figure 3D:
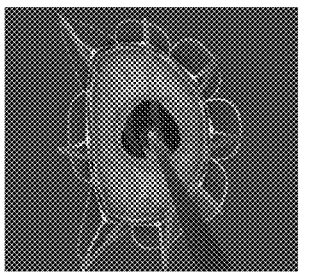
FIG. 3D is a top view of the prosthetic heart valve of FIG. 3A showing the atrial petals open for positioning and hemodynamic function verification.

FIGS. 3A-3F show an exemplary method for controllably delivering an expandable mitral valve with a double frame of an embodiment of the present invention. FIG. 3A shows the approach to the mitral valve. FIG. 3B shows unsheathing of the ventricular skirt. FIG. 3C shows controlled expansion of the frame, allowing repositioning or re-sheathing by contracting the frame. FIG. 3D shows the atrial petals open for positioning and hemodynamic function verification. Repositioning can be achieved by contracting the frame. Re-sheathing can be achieved by contracting the frame and bringing in the petals with control wires. FIG. 3E shows two views of releasing the control wires in the final position. FIG. 3F shows two views of removing the guide wire and final verification of the valve position and function.

In some embodiments, the steps described in FIGS. 3A-3F may be used to deploy the valve, in the proposed sequence or in another sequence of steps. The delivery may be transatrial, trans-apical, venous, trans-septal or any other vascular or non-vascular route. In one embodiment the system may be electromechanical and computer controlled in order to facilitate the steps for delivery, deployment, anchoring, re-sheathing and release.

FIGS. 3G-3L show a method for controlled re-sheathing of an expandable mitral valve with petals of an embodiment of the present invention. FIG. 3G illustrates how a single button operation minimizes complexity in re-sheathing atrial petals after deployment. FIG. 3H shows how control wires pass outside or within slots in atrial petals to enable inward deflection. FIG. 3I shows coordinated contraction of stent and forward motion of sheath allow for petals to be retracted into the frame. FIG. 3J shows that at minimum driven size, the sheath moves forward and can pass over a funneled ventricular skirt. FIG. 3K shows a super-elastic nitinol tip that forms a funnel to reduce friction, and that the structure from a multi-lumen tube allows the use of wires to pull petals inward without damaging the tip. FIG. 3L shows the nitinol tip recoils into a straight configuration after passing over the implant.

Therefore, in some embodiments, the valve maybe fully repositioned or re-sheathed as shown in the method illustrated in FIGS. 3G-3L. In order to re-sheath the heart valve device, in some embodiments the control wires of the delivery device maybe used to deflect the petals or other anchoring members in order to re-sheath them. In one embodiment, the control wires will pass on the outside of the ventricular or atrial petals, so that so they can be used to deform inward those petals, or other anchoring elements, so that the sheath can move over them. In one embodiment, guide elements or channels on the petals or control wires may be used so as to allow mechanical deflection without the wires slipping on the surface of the petals. In some embodiments, those petals may be covered by a cloth or other surface coating which may interfere with forward sheath motion when moving forward over the petals or other anchoring elements. In such cases, the control with other elongated elements from the delivery device may be used to bend in preferential directions the cloth or other surface in order to minimize interference with the motion of the sheath. In other embodiments, other types of mechanical elements, including but not limited to wires, rods and hooks, may extend from the delivery device and allow for inward deflection of the atrial and/or ventricular petals and/or other anchoring elements in order to minimize interference with sheath in the re-sheathing process.

In some embodiments, the guide tip can have a shape or slit on its surface to interfere with the tip of the sheath. In some embodiments, the tip of the sheath has a trumpet or expanded shape, which can be collapsed and sustained in the collapsed state by mechanical interference with the guide tip. As the sheath is retracted during deployment and interference is lost with the guide tip, the distal end of the sheath expands, which allows for easier re-sheathing of the implant. An expandable sheath tip will also allow reduction of the re-sheathing force and decrease interference when the sheath moves over the petals or anchoring elements of the implant.

In some embodiments, the actuator elements can be independently controlled in order to generate desired shape changes in the inner and/or outer frame. In some embodiments, actuators on the anterior section of the external frame can be controlled independently of actuators in the posterior section of the outer frame. In this embodiment, during expansion the user may preferentially expand the anterior section of the frame to achieve the correct inter-trigonal length and expand the posterior section of the frame in order to have an improved fit and seal of the elements against the tissue.

Many modifications of the embodiments of the present disclosure will come to mind to one skilled in the art to which the disclosure pertains upon having the benefit of the teachings presented herein through the foregoing descriptions and the associated drawings. Therefore, it is to be understood that the present invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of implanting a prosthetic heart valve, comprising:
    advancing a prosthetic heart valve to an implantation location within a patient's body, wherein the prosthetic heart valve is in a first radially contracted configuration and is releasably coupled to a delivery apparatus;
    positioning the prosthetic heart valve within a native heart valve annulus;
    expanding a frame of the prosthetic heart valve from the first radially contracted configuration to a first radially expanded configuration by actuating the delivery apparatus;
    contracting the frame of the prosthetic heart valve from the first radially expanded configuration to a second radially contracted configuration by actuating the delivery apparatus;
    repositioning the prosthetic heart valve within the native heart valve annulus while the frame of the prosthetic heart valve is in the second radially contracted configuration;
    expanding the frame of the prosthetic heart valve from the second radially contracted configuration to a second radially expanded configuration by actuating the delivery apparatus; and
    releasing the prosthetic heart valve from the delivery apparatus while the prosthetic heart valve is in the second radially expanded configuration, wherein releasing the prosthetic heart valve from the delivery apparatus results in radial expansion of a flange portion of the prosthetic heart valve, wherein the flange portion comprises a plurality of petals, wherein the delivery apparatus comprises a plurality of control wires disposed radially outwardly from the petals when the prosthetic heart valve is releasably coupled to the delivery apparatus, and wherein the petals expand radially outwardly beyond the control wires when the prosthetic heart valve is released from the delivery apparatus.

2. The method of claim 1, wherein contracting the frame occurs while the prosthetic heart valve is disposed outside of a sheath of the delivery apparatus.

3. The method of claim 2, wherein actuating the delivery apparatus includes moving one or more actuation wires of the delivery apparatus relative to the frame of the prosthetic heart valve.

4. The method of claim 3, wherein the frame of the prosthetic heart valve includes one or more actuation members coupled to the frame, and wherein each of the actuation wires of the delivery apparatus is coupled to a respective actuation member of the prosthetic heart valve.

5. A method of implanting a prosthetic heart valve, comprising:
    advancing a prosthetic heart valve through a patient's vasculature with a delivery apparatus such that the prosthetic heart valve is disposed in or adjacent a native heart valve;
    deploying the prosthetic heart valve from a sheath of the delivery apparatus;
    expanding a frame of the prosthetic heart valve from a radially contracted configuration to a radially expanded configuration, wherein the prosthetic heart valve comprises one or more flanges that are retained in an at least partially radially contracted configuration by control wires of the delivery apparatus;

contracting the frame of the prosthetic heart valve from the radially expanded configuration to an at least partially radially contracted configuration;

moving the prosthetic heart valve relative to the native heart valve annulus while the frame of the prosthetic heart valve is in the at least partially radially contracted configuration;

re-expanding the frame of the prosthetic heart valve from the at least partially radially contracted configuration to the radially expanded configuration;

releasing the prosthetic heart valve from the delivery apparatus by releasing the control wires from the prosthetic heart valve; and after releasing the prosthetic heart valve from the control wires of the delivery apparatus, expanding the one or more flanges of the prosthetic heart valve from the at least partially radially contracted configuration to a radially expanded configuration.

6. The method of claim 5, wherein contracting the frame occurs while the prosthetic heart valve is radially outside and axially spaced from the sheath of the delivery apparatus.

7. The method of claim 5, wherein the one or more flanges of the prosthetic heart valve include an atrial flange having a plurality of atrial petals configured to engage native tissue on an atrial side of a native mitral valve.

8. The method of claim 7, wherein the control wires are disposed radially outwardly from the atrial petals while the prosthetic heart valve is coupled to the delivery apparatus, and wherein the one or more control wires are configured to radially compress the atrial petals while the prosthetic heart valve is coupled to the delivery apparatus.

9. The method of claim 5, wherein the one or more flanges of the prosthetic heart valve include a ventricular flange configured to engage native tissue on a ventricular side of a native mitral valve.

10. The method of claim 9, wherein the control wires are disposed radially outwardly from the ventricular flange while the prosthetic heart valve is coupled to the delivery apparatus, and wherein the one or more control wires are configured to radially compress the ventricular flange while the prosthetic heart valve is coupled to the delivery apparatus.

* * * * *